(12) United States Patent
Cachia

(10) Patent No.: US 8,747,480 B2
(45) Date of Patent: Jun. 10, 2014

(54) CATHETER DELIVERABLE FOOT IMPLANT AND METHOD OF DELIVERING THE SAME

(76) Inventor: Victor V. Cachia, San Juan Capistrano, CA (US)

(*) Notice: Subject to any disclaimer, the term of this patent is extended or adjusted under 35 U.S.C. 154(b) by 0 days.

(21) Appl. No.: 13/164,612

(22) Filed: Jun. 20, 2011

(65) Prior Publication Data

US 2012/0130501 A1    May 24, 2012

Related U.S. Application Data

(63) Continuation of application No. 12/325,894, filed on Dec. 1, 2008, now abandoned, which is a continuation of application No. 11/068,675, filed on Mar. 1, 2005, now abandoned.

(60) Provisional application No. 60/549,767, filed on Mar. 3, 2004.

(51) Int. Cl.
*A61F 2/42* (2006.01)
*A61B 17/58* (2006.01)

(52) U.S. Cl.
USPC .......................... 623/21.18; 606/62

(58) Field of Classification Search
USPC ........................... 623/21.18–21.19
See application file for complete search history.

(56) References Cited

U.S. PATENT DOCUMENTS

| | | | |
|---|---|---|---|
| 4,229,839 A | 10/1980 | Schwemmer | |
| 4,932,969 A | 6/1990 | Frey et al. | |
| 5,228,454 A | 7/1993 | Siegler | |
| 5,344,459 A | 9/1994 | Swartz | |
| 5,360,450 A | 11/1994 | Giannini | |
| 5,531,792 A | 7/1996 | Huene | |
| 5,591,199 A | 1/1997 | Porter et al. | |
| 5,669,909 A | 9/1997 | Zdeblick et al. | |
| 5,888,220 A * | 3/1999 | Felt et al. | 128/898 |
| 5,957,953 A | 9/1999 | DiPoto et al. | |
| 6,099,531 A | 8/2000 | Bonutti | |
| 6,132,468 A | 10/2000 | Mansmann | |
| 6,136,032 A | 10/2000 | Viladot Perice et al. | |
| 6,168,631 B1 | 1/2001 | Maxwell et al. | |
| 6,280,456 B1 | 8/2001 | Scribner et al. | |
| 6,436,146 B1 | 8/2002 | Hassler et al. | |
| 6,443,988 B2 | 9/2002 | Felt et al. | |
| 2001/0049527 A1 * | 12/2001 | Cragg | 606/61 |
| 2003/0199979 A1 * | 10/2003 | McGuckin, Jr. | 623/17.11 |
| 2004/0167631 A1 | 8/2004 | Luchesi et al. | |
| 2005/0175703 A1 | 8/2005 | Hunter et al. | |
| 2005/0177165 A1 | 8/2005 | Zang et al. | |
| 2005/0229433 A1 | 10/2005 | Cachia | |

OTHER PUBLICATIONS

Green et al, *Assessing the Pros and Cons of Subtalar Implants*, May 2006, Podiatry Today, vol. 19, Issue 5.

(Continued)

*Primary Examiner* — David Isabella
*Assistant Examiner* — Ann Schillinger
(74) *Attorney, Agent, or Firm* — Knobbe, Martens, Olson & Bear, LLP

(57) ABSTRACT

Methods and devices are disclosed for manipulating alignment of the foot to treat patients with flat feet, posterior tibial tendon dysfunction and metatarsophalangeal joint dysfunction. An inflatable implant is positioned in or about the sinus tarsi and/or first metatarsal-phalangeal joint of the foot. The implant is insertable by minimally invasive means and inflatable through a catheter or needle. Inflation of the implant alters the range of motion in the subtalar or first metatarsal-phalangeal joint and changes the alignment of the foot.

1 Claim, 30 Drawing Sheets

(56) References Cited

OTHER PUBLICATIONS

Aetna, *Clinic Policy Bulletin: Subtalar Implant for Treatment of Flatfoot Deformity*, Aug. 22, 2003.

Dockery, et al., "*The Maxwell-Brancheau Arthroereisis (MBA) Implant in Pediatric and Adult Flexible Flatfoot Conditions,*"Foot and Ankle Quarterly, vol. 12, No. 4, pp. 107-120, Winter 1999.
Frey et al., *Diagnosis: Arthroscopy deconstructs sinus tarsi diagnosis,*,Feb. 1999, BioMechanics.

* cited by examiner

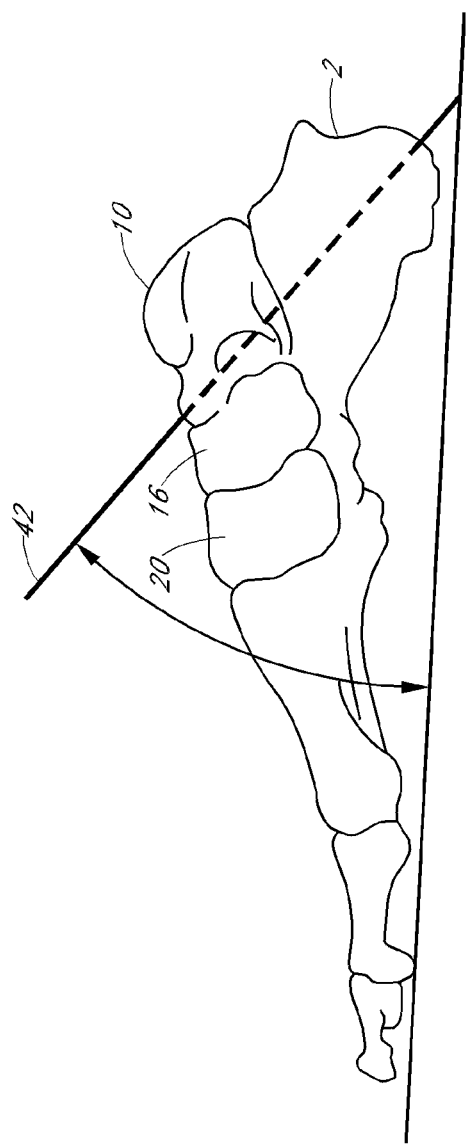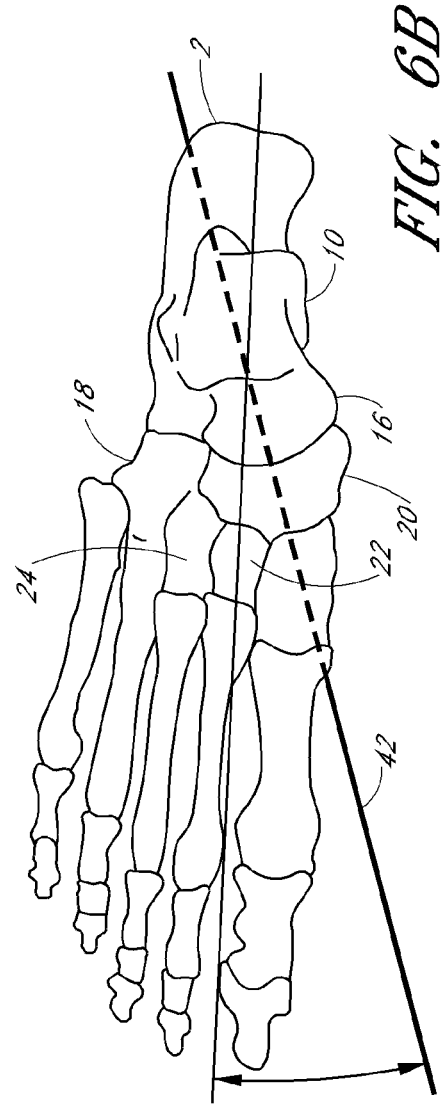

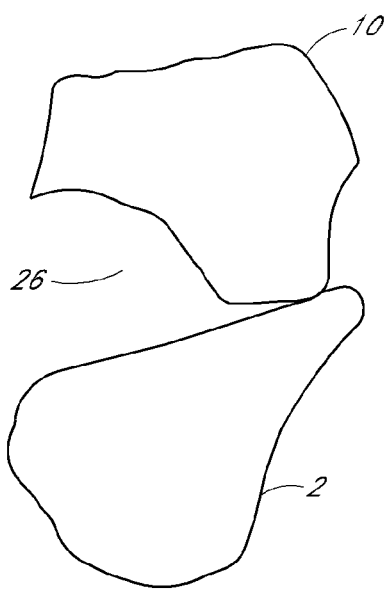 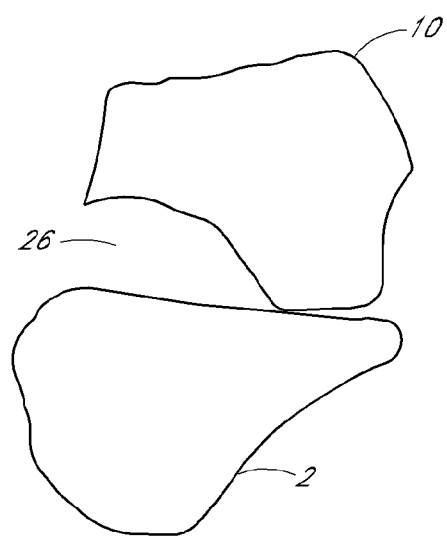
FIG. 18A   FIG. 18B
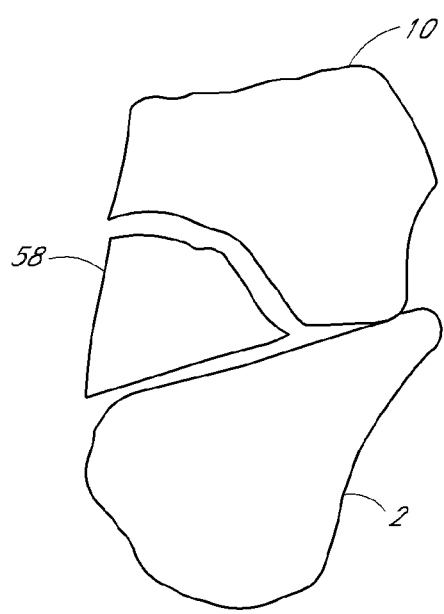 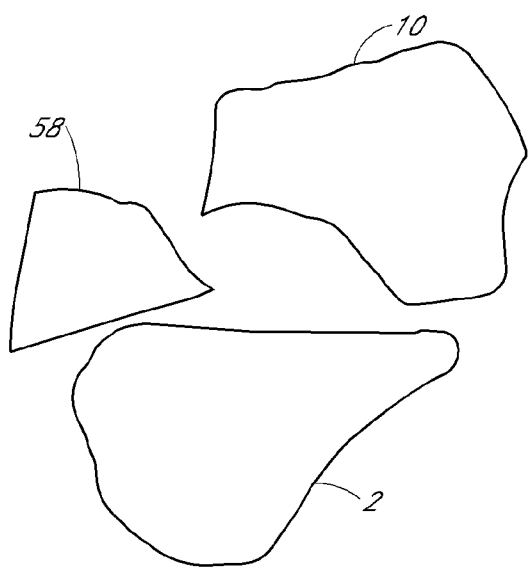
FIG. 18C   FIG. 18D

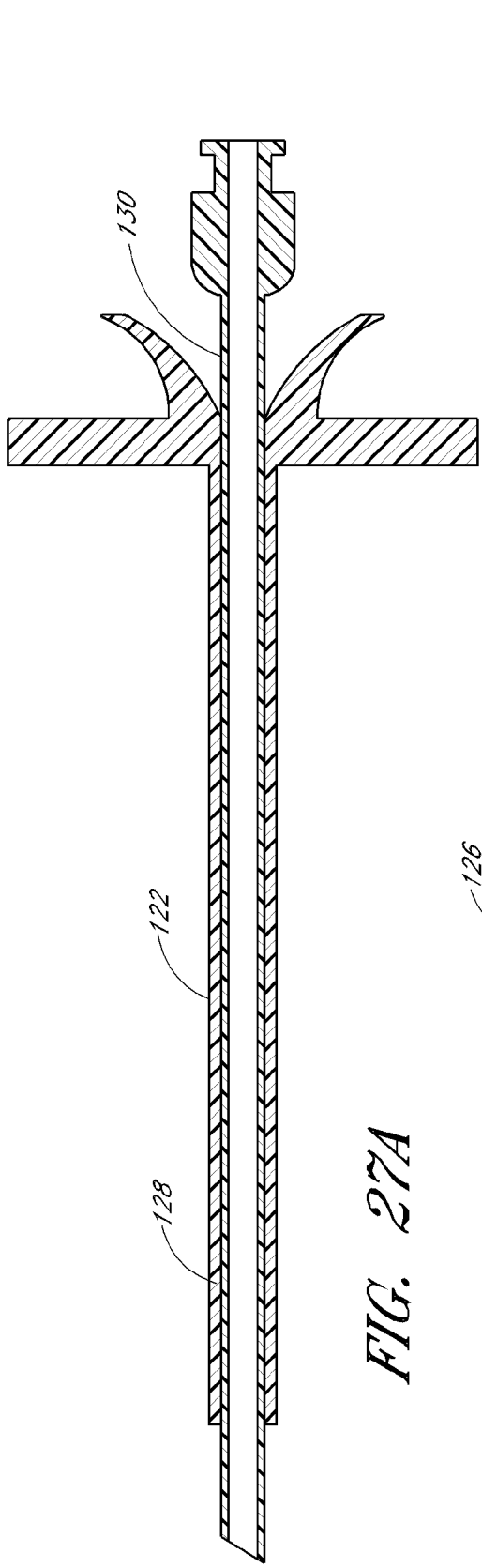
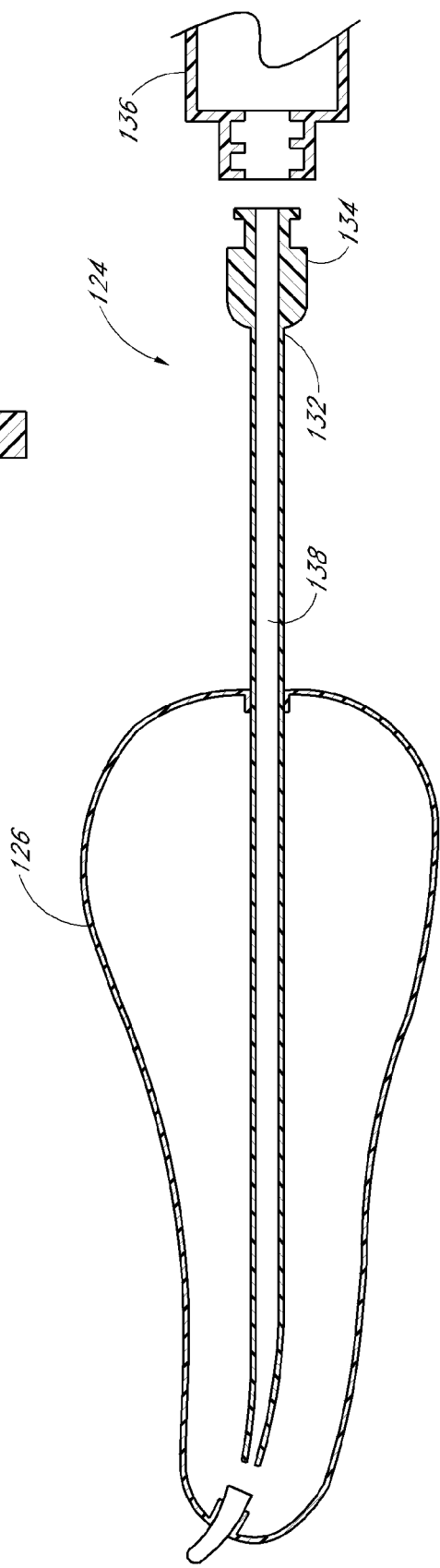
FIG. 27A
FIG. 27B

CATHETER DELIVERABLE FOOT IMPLANT AND METHOD OF DELIVERING THE SAME

CROSS-REFERENCE TO RELATED APPLICATIONS

The present application is a continuation of U.S. patent application Ser. No. 12/325,894 filed on Dec. 1, 2008, now abandoned which is a continuation of U.S. patent application Ser. No. 11/068,675 filed on Mar. 1, 2005, now abandoned which claims priority under 35 U.S.C. §119(e) to U.S. Provisional Application No. 60/549,767 filed on Mar. 3, 2004, the disclosure of which are incorporated by reference herein in its entirety.

BACKGROUND OF THE INVENTION

1. Field of the Invention

This invention relates generally to the field of subtalar joint and first metatarsal-phalangeal implants for treating foot conditions including flat feet, adult posterior tibial tendon dysfunction and metatarsophalangeal joint dysfunction.

2. Description of the Related Art

Pes valgo planus, or flat foot, is a common condition where the arch of a foot is weakened and is unable to properly support the weight of the body. With a flat foot, shock absorption is reduced and misalignment of the foot occurs. These changes may eventually result in foot and ankle pain, tendonitis, plantar fasciitis and hallux valgus, hallux limitus and functional disorders of the knees, hips and back. Although there are several causes of flat feet, one frequent cause is excessive motion in the subtalar joint of the foot.

As early as 1946, surgeons have been attempting to apply the arthroereisis concept to the subtalar joint. Arthroereisis is a surgical procedure for limiting motion in a joint in cases of excessive mobility. One early method was to remedy abnormal excursion of the talus on the calcaneus with the talus contacting the floor of the sinus tarsi by using an "abduction block" procedure. During the abduction block procedure, a wedge-shaped bone graft was impacted into the anterior leading edge of the posterior facet of the calcaneus. Impacting such a bone graft prevented excessive inferior displacement of the talus upon the calcaneus, thus limiting the amount of excess pronation of the subtalar joint.

A pronation limiting osteotomy in the form of a lateral opening wedge of the posterior facet was developed for treatment of "flatfoot" in cerebral palsy patients in 1964. In order to prevent interfering with subtalar joint motion, a wedge-like bone graft was used to improve the weight-bearing alignment of the calcaneus. In 1970, an accessory bone graft placed in the sinus tarsi was developed as a corrective procedure. Later, the bone graft was replaced with a silastic plug. As early as 1976, a high molecular weight polyethylene plug was developed. The plug is cemented into the calcaneal sulcus against a resected portion of the posterior calcaneal facet. This procedure, known as "STA-peg" (subtalar arthroereisis-peg), is a commonly used subtalar joint arthroereisis procedure. STA-peg does not block excessive pronation, but rather alters the axis of motion of the subtalar joint.

In addition, in 1976, a high molecular weight, polyethylene, threaded device known as a "Valenti Sinus Tarsi Arthroereises Device" was invented. The procedure used to implant the Valenti device is commonly referred to as the "Valenti" procedure. Unlike the STA-peg procedure, the Valenti procedure is an extra-articular procedure that involves placing the Valenti device into the sinus tarsi to block the anterior and inferior displacement of the talus. Such placement of the Valenti device does not restrict normal subtalar joint motion, but does block excessive pronation and resulting sequelae. The Valenti device has a frusto-conical shape and threads on the outer surface of the device, which allow it to be screwed into the sinus tarsi. Because of the shape of the Valenti device, the greater the penetration of the device into the sinus tarsi, the more the sinus is dilated and the more calcaneal eversion is eliminated.

However, several problems reduce the desirability of the Valenti procedure and device. Because of its frusto-conical shape and the manner in which it is inserted, the Valenti device is difficult to precisely position in the subtalar joint and difficult to ensure that the proper amount of calcaneal eversion has been eliminated. Furthermore, it is generally difficult to locate the device properly within the tarsal canal because the implant must be threaded at least 3 to 5 millimeters medial to the most lateral aspect of the posterior facet for correct placement. Because of its polyethylene construction, the device cannot be imaged using radiography (X-ray) to determine whether the proper position has been achieved.

More recent attempts to control subtalar motion in the hyperpronated foot include the Maxwell-Brancheau arthroereisis (MBA), the Kalix subtalar prosthesis and the Futura arthroereisis. The MBA is a titanium alloy implant where the implantation procedure involves insertion "trial" implants to determine the proper size of the actual implant used. The MBA implant procedure requires either general anesthesia or local anesthesia with sedation. It also requires up to a ¾ inch incision on the lateral portion of the foot. The MBA implant uses a metal guide pin for positioning the implant. The guide pin must be positioned with extreme care to prevent damage to the calcaneus. A two-week period of crutch use and foot immobilization typically follows the procedure. The Kalix implant is a cone-shaped implant with limited expansion ability. The operator can use a double screwdriver to increase the diameter of the implant. The Kalix implant requires two weeks of non-weight bearing and three to four weeks of immobilization following implantation of the device.

Another site of frequent foot problems is the first metatarsal-phalangeal joint. The first metatarsal-phalangeal joint (MTP) is a complex joint of the foot where bones, tendons and ligaments work together to transmit and distribute the body's weight, especially during movement. Bunions are the first MTP joint disorder most frequently treated by podiatric surgeons. First-line treatment involves educating patients about the condition and evaluating their footwear. Providers can direct their patients to wear wider, low-heeled shoes, use bunion pads, apply ice and take over-the-counter analgesic medications. These options are designed to relieve pain and make it easier to walk and engage in physical activities, but they do not address the underlying cause of bunions.

Bunions usually occur from inherited faulty biomechanics that put abnormal stress on the first MTP joint. Contrary to popular belief, bunions are aggravated, not caused, by shoes. Various non-surgical approaches can help prevent aggravation of bunions and other MTP-related problems. For some patients, non-surgical treatment is sufficient, but surgical intervention is considered if the bunions are progressive or if non-operative treatments provide inadequate improvement.

Bunion surgery is performed to repair tendons and other soft tissue and remove a small amount of bone. Procedures to correct more severe bunions may involve removal of the bump or minor realignment of the big toe joint. The most severe and disabling bunions often require extensive joint realignment, reconstruction, implants or joint replacement. Significant morbidity and recuperation time is required for such procedures.

First MTP-related problems also occur from repetitive trauma to the area and from arthritis. Over time, active persons can put continuous stress on the first MTP joint that eventually wears out the cartilage and lead to the onset of arthritis. This condition, known as hallux rigidus, causes loss of movement and pain in the joint. In most situations, non-operative treatments can be prescribed to provide relief, but those with advanced disease might need surgery, especially when the protective covering of cartilage deteriorates, leaving the joint damaged and with decreased range of motion. Again, significant morbidity results from these procedures and an extended recovery time is required.

SUMMARY OF THE INVENTION

In one embodiment, the invention is a subtalar joint implant, comprising an inflatable balloon adapted for positioning in the sinus tarsi of a foot. In another embodiment, the invention is a foot implant comprising an inflatable balloon, wherein the inflatable balloon is adapted for extra-articular positioning in the sinus tarsi of the foot.

In one embodiment of the invention, a method for treating a patient is provided. The method comprises providing an inflatable subtalar implant for the procedure, inserting the implant into the sinus tarsi of a food, inflating the implant with an inflation material and changing the alignment of the hindfoot. Furthermore, the insertion of the implant into the sinus tarsi may be performed through a cannula inserted into the sinus tarsi. The inflation material may be a fluid or a solid. One example of a solid inflation material are microspheres. In other embodiments of the invention, multiple agents may be used to inflate the implant, such as a substrate and catalyst capable of solidifying. In some embodiments, the multiple agents are combined before inflation of the implant. In other embodiments, the multiple agents are combined during inflation of the implant.

In another embodiment of the invention, another method for treating a patient is provided. This method comprises providing an inflatable subtalar implant for the procedure, identifying a foot having a first range of motion, inserting the implant into the sinus tarsi of the foot and adapting the foot to a second range of motion by inflating the implant.

In still another embodiment of the invention, another method for treating a patient is provided. This method comprises providing an inflatable subtalar implant, identifying a foot having a first weight-bearing alignment, changing the foot to a second weight-bearing alignment, inserting the implant into the sinus tarsi of the foot and securing the foot in the second weight-bearing alignment by inflating the implant. The first and second weight-bearing alignments may be defined by the angle formed between a first line connecting the edges of an articular surface of the talus and a second line connecting the edges of an articular surface of a navicular bone. Alternatively, the first and second weight-bearing alignments may be defined by the angle between the long axis of the talus and a second line along the long axis of the first metatarsal bone. Still another alternative is to define the first and second weight-bearing alignments by the angle between the first line between most plantar point of a calcaneus and the most inferior point of the distal articular surface of the calcaneus, and a second line within a horizontal plane of the patient. Still another alternative is to define the first and second weight-bearing alignments by the angle between a first line along the plantar border of the calcaneus and a second line along a first midpoint in the body of a talus and a second midpoint in the neck of the talus.

Several embodiments of the invention provide a minimally invasive method for treating a patient. This method comprises providing an inflatable subtalar implant, inserting the implant into the sinus tarsi of a foot, inflating the implant, changing the range of motion of the subtalar joint of the foot and conforming the implant to the shape of the sinus tarsi thereby.

Some embodiments of the invention provide a method for treating a patient, comprising identifying a cyma line in a foot of a patient, smoothing the cyma line and securing the smoothing by inflating an implant in the sinus tarsi of the foot.

In another embodiment of the invention, a method for treating a patient is provided, comprising accessing the sinus tarsi of a foot through an access path having a cross sectional diameter of no more than about 0.5 inches, where the sinus tarsi have a talus and calcaneus spaced apart by a first minimum distance. The space between the talus and calcaneus is increased to a second minimum distance and the talus and calcaneus is then restrained at the second minimum distance.

In another embodiment, another method for treating a patient is provided, comprising providing an inflatable first metatarsal-phalangeal joint implant, inserting the implant into a first metatarsal-phalangeal joint of a foot and inflating the implant with a fluid.

Several embodiments of the invention provide these advantages, along with others that will be further understood and appreciated by reference to the written disclosure, figures, and claims included herein.

BRIEF DESCRIPTION OF THE DRAWINGS

The structure and method of making the invention will be better understood with the following detailed description of embodiments of the invention, along with the accompanying illustrations, in which:

FIGS. 6A and 6B depict the axis of rotation for the subtalar joint;

FIGS. 18A and 18B are schematic coronal cross-sectional views of a neutrally aligned and hyperpronated foot, respectively. FIG. 18C is a schematic view depicting the effect of material placed within the sinus tarsi. FIG. 18D is a schematic view depicting the tendency of the talus and calcaneus to cause displacement of material in the sinus tarsi;

FIGS. 27A through 27C depict one embodiment of the delivery system;

FIG. 30A shows an uninflated implant attached to the delivery catheter and FIG. 30B depicts an inflated implant with the delivery catheter removed;

DETAILED DESCRIPTION OF THE PREFERRED EMBODIMENT

Figure 1:
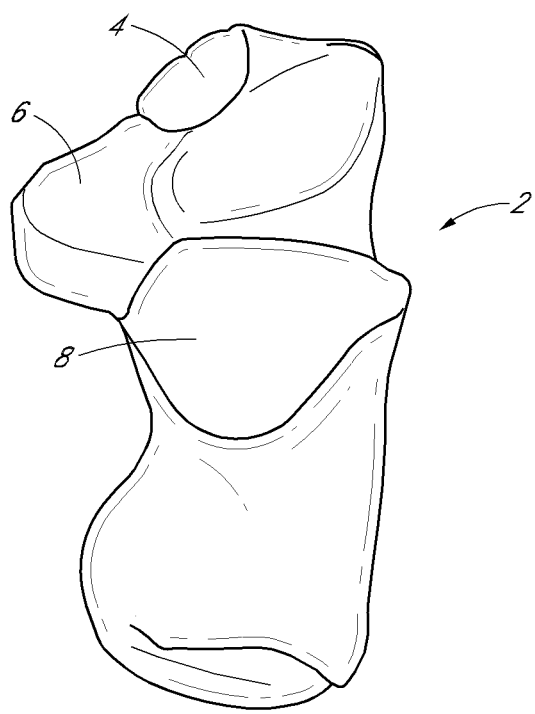
FIG. 1 is a superior elevation view of the calcaneus.
Figure 2:
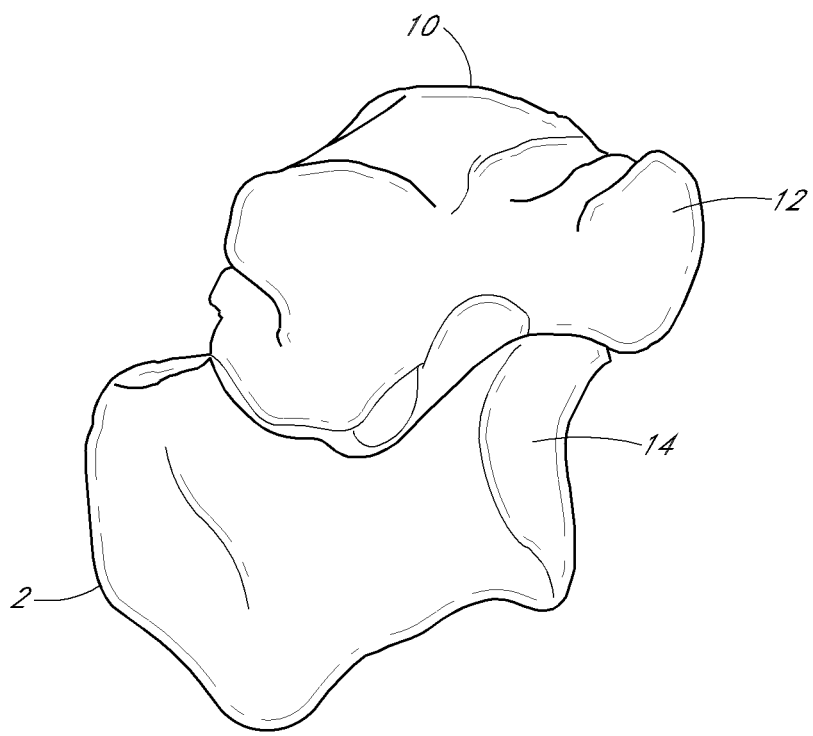
FIG. 2 is a lateral elevation view of the talo-calcaneus relationship.
Figure 3:
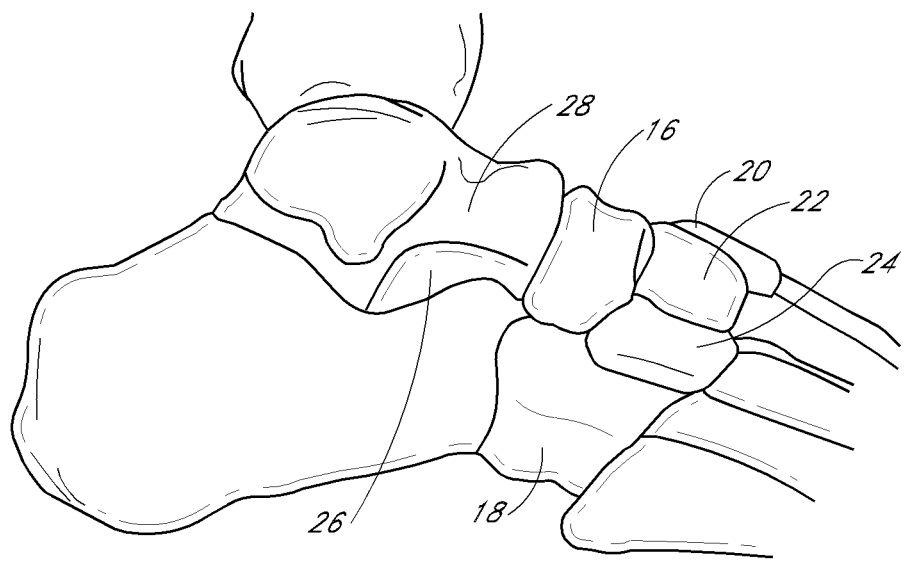
FIG. 3 is a lateral elevation view of the foot bones showing the sinus tarsi.
Figure 4:
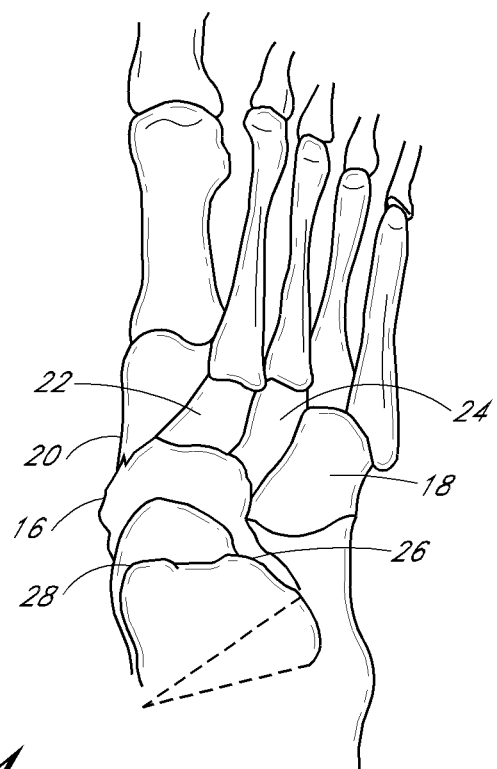
FIG. 4 is dorso-plantar elevation view of the foot showing the outline of the sinus tarsi.

The talus and calcaneus form the bones of the hindfoot. The talus is a bone with no muscular attachments, but is stabilized by ligaments and cradled by the tendons passing from the leg to the foot. As shown in FIG. 1, the calcaneus 2 articulates with the talus at the calcaneal anterior 4, middle 6 and posterior facets 8. FIG. 2 depicts the relationship between the talus 10 and calcaneus 2 and the talo-calcaneal surfaces 12, 14 that articulate with the midfoot bones. FIGS. 3 and 4 depict the midfoot bones, including the navicular 16, cuboid 18 and cuneiform bones 20, 22, 24. The sinus tarsi 26, also known as the talocalcaneal sulcus, is an extra-articular anatomic space between the inferior neck 28 of the talus 10 and the superior aspect of the distal calcaneus 2. The space continues with the tarsal canal, a funnel or trumpet-shaped space that extends medially to a small opening posterior to the sustentaculum tali. Sinus tarsi 26 is oriented obliquely from a lateral distal opening to proximal medial end. The canal is wider laterally and narrower medially, but the lateral opening of the canal is capable of widening with foot supination and narrowing with pronation. Fat and ligaments occupy the space and are perfused by the tarsal canal artery, a branch of the posterior tibial artery.

Figure 5A:
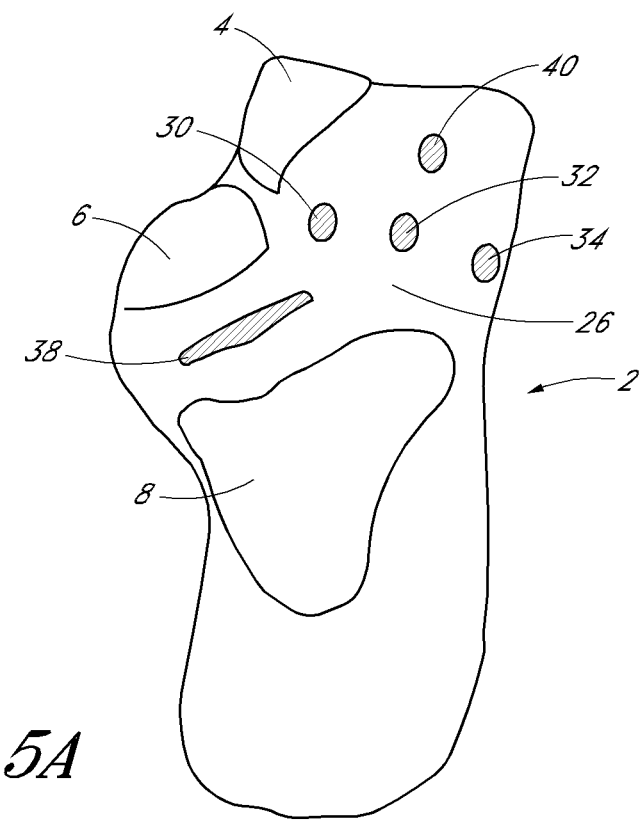
FIG. 5A is a superior elevation view of the ligament attachment sites to the calcaneus.
Figure 5B:
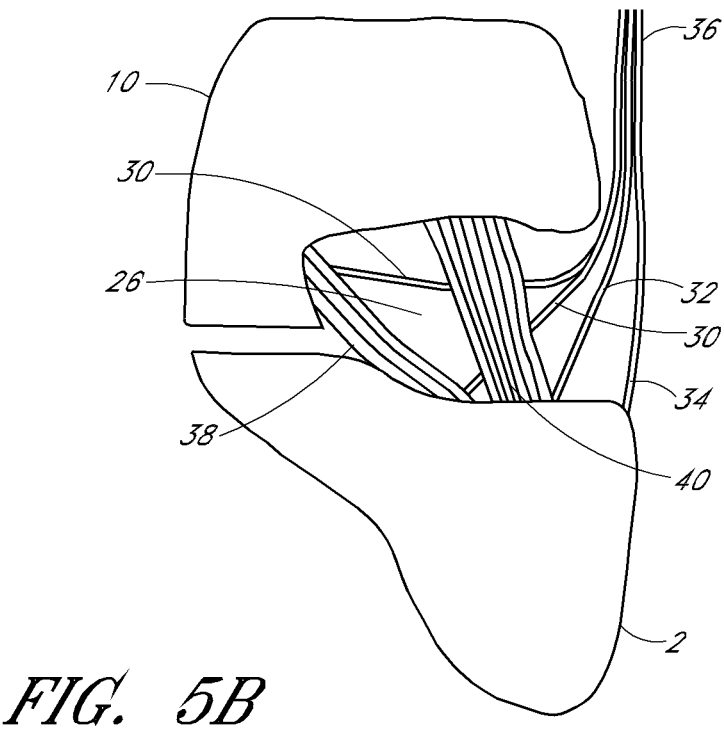
FIG. 5B is a coronal cross-section view showing the ligaments of the sinus tarsi.

FIG. 5A is a superior view of the calcaneus 2 showing the ligament attachments within the tarsal canal, including the inferior attachments 30, 32, 34 of the extensor retinaculum 36 of the foot, the interosseous talocalcaneal ligament 38 and the cervical ligament 40. The primary ligament is interosseous talocalcaneal ligament 38, shown in a coronal cross section of the foot in FIG. 5B. Its primary function is to maintain apposition of the talus 10 to the calcaneus 2. The interosseous talocalcaneal ligament 38 is anterior to the posterior subtalar joint and extends from calcaneus 2 to talus 10. It forms a transverse partition between the sulcus tali and the sulcus calcaneus, the two grooves forming the sinus tarsi. Interosseus ligament 38 separates anterior 4 and middle facets 6 of the calcaneal portion of the anterior subtalar joint from the posterior facet 8 of the posterior subtalar joint and provides stability to the hindfoot. The cervical ligament 40, like the other ligaments of the tarsal sinus 26, is extra-capsular. Cervical ligament 40 is larger than interosseous talocalcaneal ligament 38. It attaches to the cervical tubercle of the inferior and lateral aspects of neck 28 of talus 10 and the dorsal aspect of calcaneus 2 medial to the origin of the extensor digitorum brevis muscle. Cervical ligament 40 is flattened, its width being four times greater than its thickness. The primary function of cervical ligament 40, along with interosseous talocalcaneal ligament 38, is to limit inversion of the hindfoot. The inferior extensor retinaculum 36 is a Y-shaped strap of flat thick connective tissue that crosses the proximal portion of the foot. The stem of the "Y" is composed of superficial and deep laminae that enclose the long extensor tendons and prevent bow stringing of the long extensor tendons. Laterally, inferior extensor retinaculum 36 is anchored to talus 10 and calcaneus 2 by ligament-like roots that are located in the tarsal sinus and canal. The medial 30, intermediate 32 and lateral roots 34 together constitute the majority of the ligamentous material in the tarsal sinus 26. Inferior extensor retinaculum 36 assists cervical ligament 40 in limiting inversion of the subtalar joint. Medial root 30 attaches to calcaneus 2 just anterior to the attachment site of interosseous talocalcaneal ligament 38. Medial root 30 has a secondary attachment site to talus 10 in common with interosseous talocalcaneal ligament 38. Intermediate root 32 attaches to calcaneus 2 posterior to the attachment site of cervical ligament 40. Lateral root 34 attaches to calcaneus 2 at the external aspect of the tarsal sinus 26.

Figure 7B:
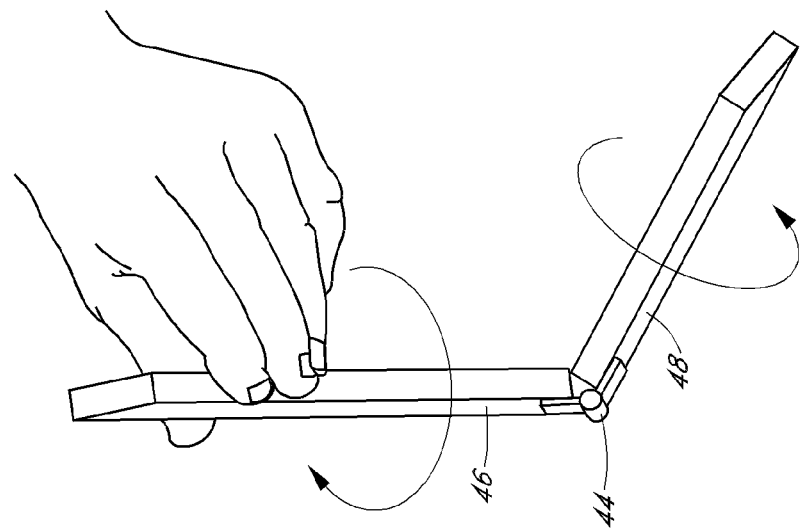
FIGS. 7A and 7B are schematic views of the motion of the subtalar joint as a mitered hinge joint.
Figure 7A:
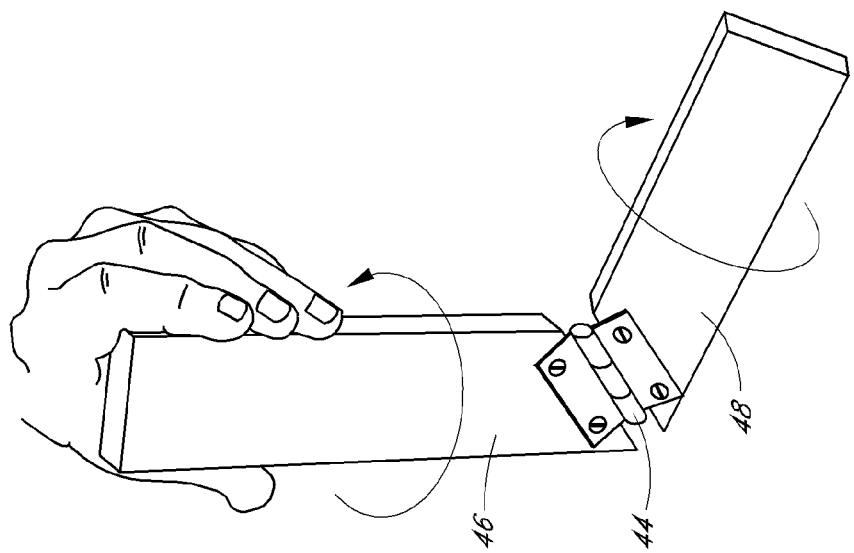
Figure 8B:
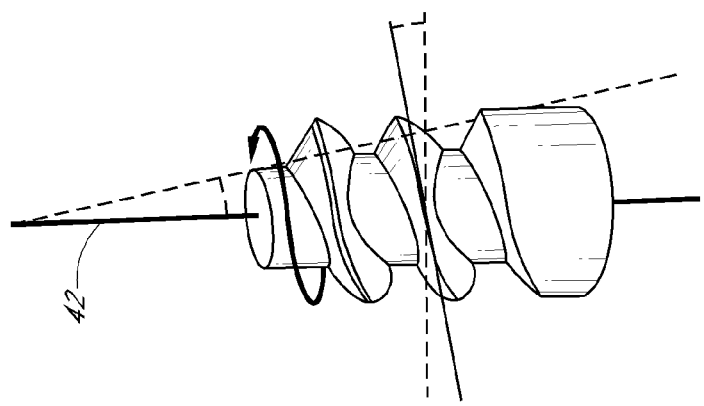
FIGS. 8A and 8B are schematic views of subtalar joint motion as a threaded screw joint.
Figure 8A:
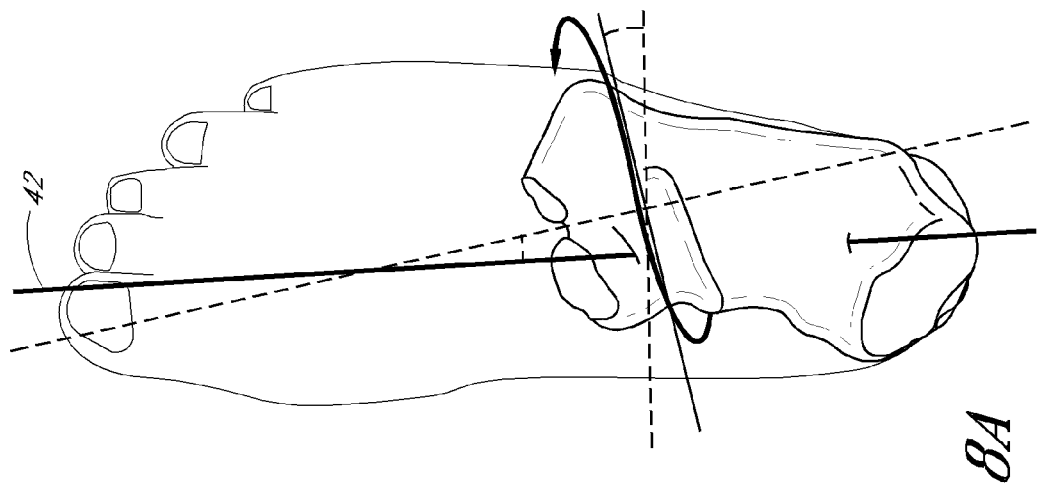

Subtalar motion is generally described as a rotational motion of the talus around the calcaneus. FIGS. 6A and 6B depict the subtalar axis of rotation 42, which typically extends upward and forward at an angle of about forty-two degrees from the floor at the heel. The axis deviates sixteen degrees medially from the midline of the foot. Generally, the subtalar joint can be inverted about twenty degrees and everted about five degrees. The average range of motion throughout the stance phase of gait, however, is only about six degrees. Longitudinal translation in both the proximal and distal directions is also associated with the rotation movement, but the direction and magnitude of this movement is highly variable in each person. Some researchers have characterized the motion of the subtalar joint as a mitered hinge joint 44, as shown in FIGS. 7A and 7B. The vertical member 46 is analogous to the leg and the horizontal member 48 is analogous to the foot. Other researchers, however, have characterized the motion of the subtalar joint as a screw joint, as shown in FIGS. 8A and 8B. The differences between the characterizations of the subtalar joint underscore the high degree of variation in the configuration of the joint within the population.

Figure 9A:
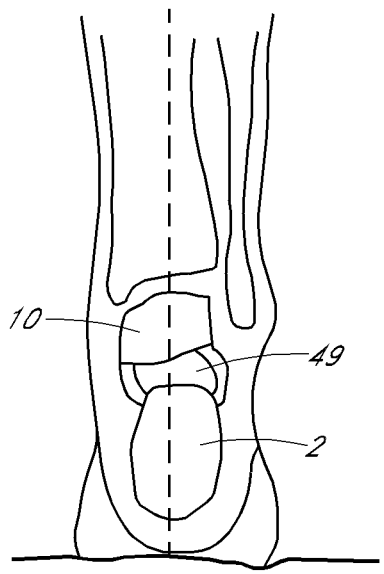
FIGS. 9A and 9B are posterior cross-sectional views of a neutrally aligned and a hyperpronated foot.
Figure 9B:
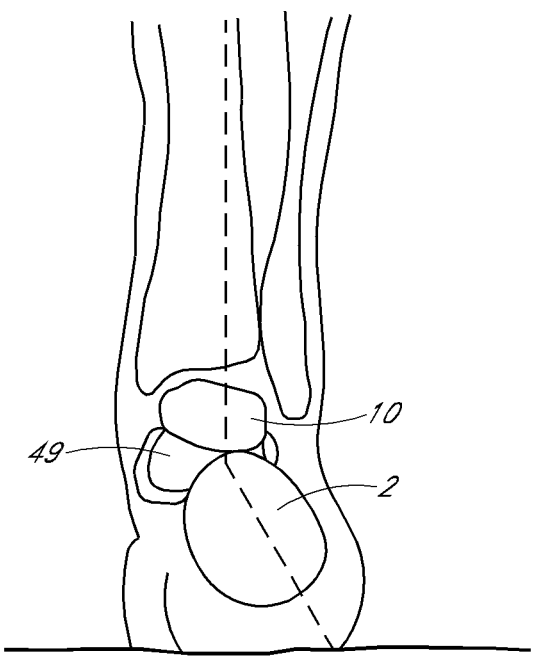

When an excessive range of motion exists in the subtalar joint, misalignment of the foot can occur. Compared to a person with a neutrally aligned foot, shown in FIG. 9A, a person with flat feet, shown in FIG. 9B, has a subtalar joint that is capable of eversion up to about six degrees from a neutral talo-calcaneal alignment. Excessive eversion places increased stress upon the foot arch. Over time, foot or ankle disorders can develop from the misalignment. Misalignment of the subtalar joint also affects the alignment of the bones in the midfoot due to the dependence of midfoot stability on hindfoot stability.

Figure 10A:
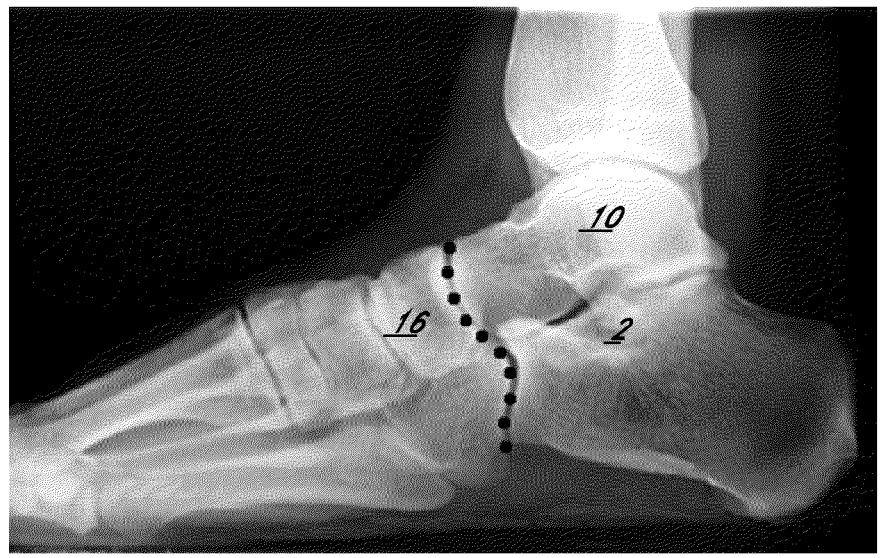
FIGS. 10A and 10B are lateral radiographs of the foot illustrating the cyma lines in a neutrally aligned and misaligned foot, respectively.
Figure 10B:
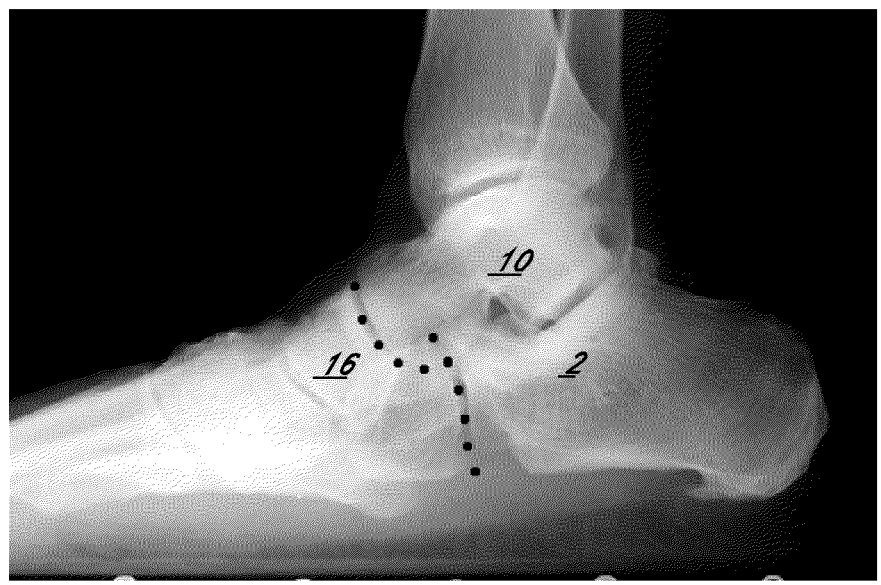
Figure 11B:
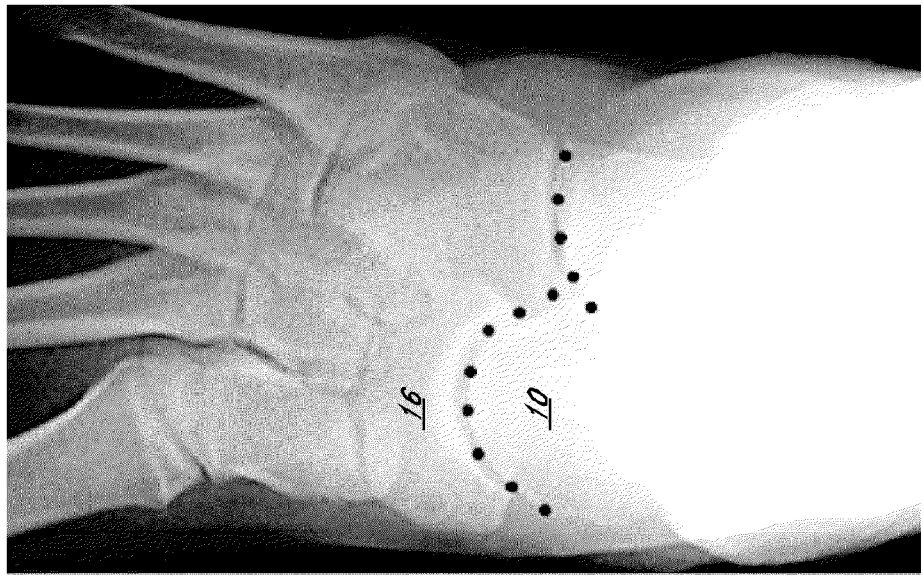
FIGS. 11A and 11B are AP radiographs of the foot illustrating the cyma lines in a neutrally aligned and misaligned foot, respectively.
Figure 11A:
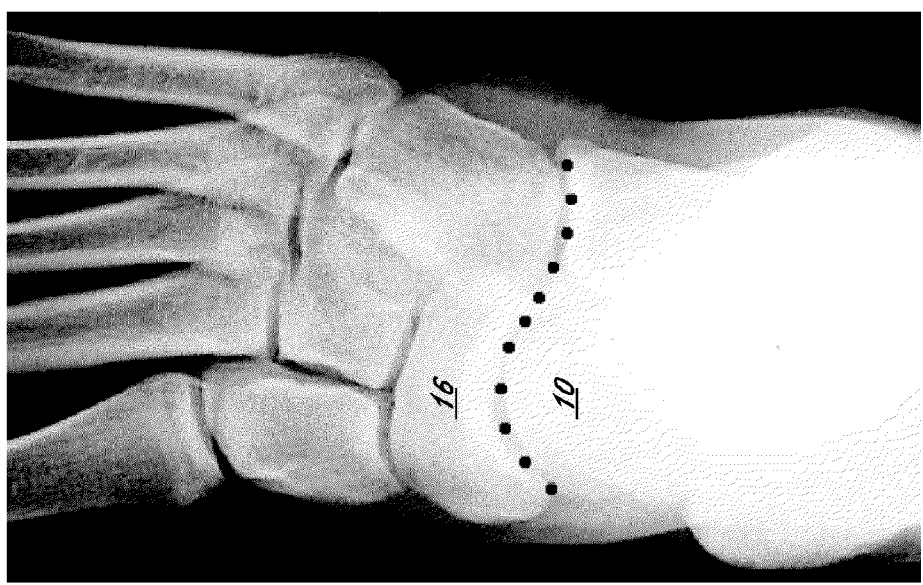

Alignment of the foot can be assessed on plain film x-ray imaging by examining the cyma lines of the foot. The term "cyma line" refers to the joining of two curved lines. A neutrally aligned foot forms a smooth cyma line (shown with dots) between the talonavicular joint and the calcaneocuboid joint on radiographs in both the lateral and AP views, as shown in FIGS. 10A and 11A, respectively. If the cyma line is broken, as shown in FIGS. 10B and 11B, this finding suggests misalignment of the talus 10 on the calcaneus 2 as seen in patients with flat feet.

Figure 12A:
FIGS. 12A and 12B are AP radiographs of the foot depicting the talonavicular coverage angles in a neutrally aligned and misaligned foot, respectively.
Figure 12B:
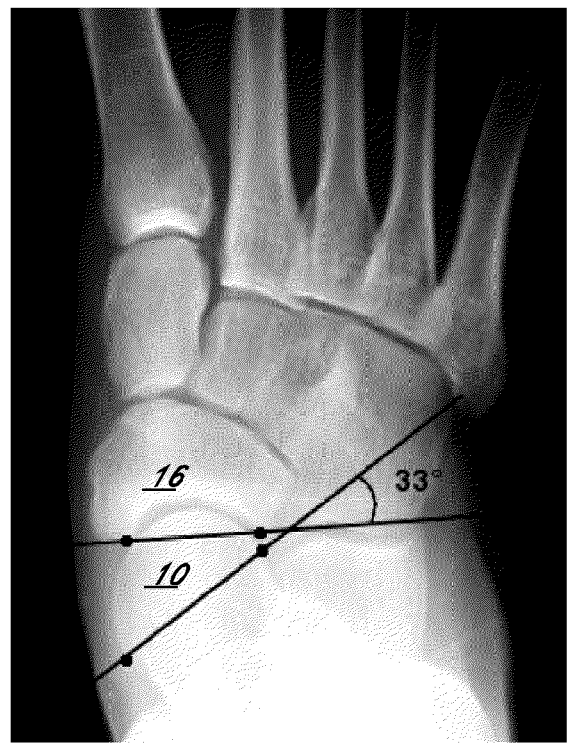
Figure 13A:
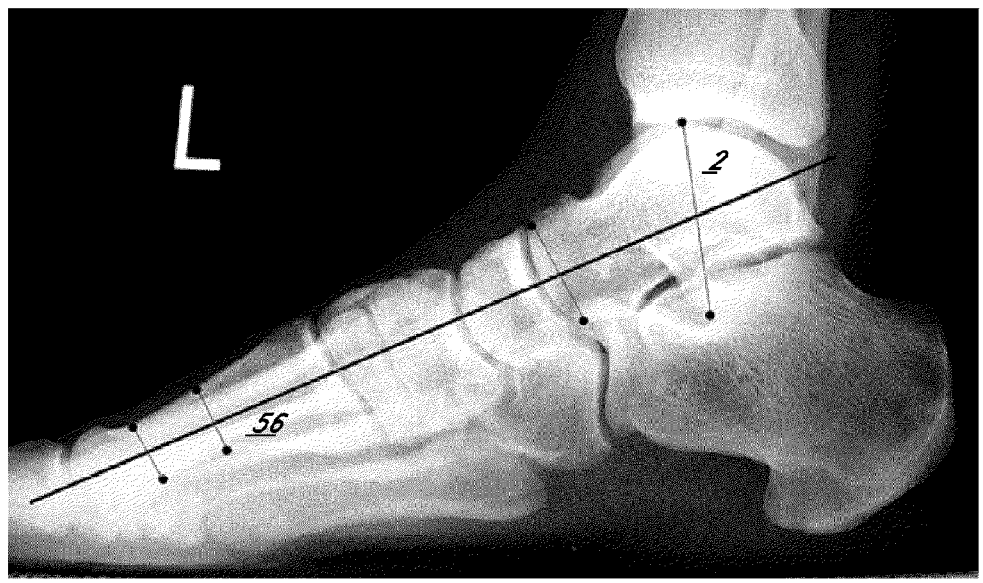
FIGS. 13A and 13B are lateral radiographs of the foot depicting lateral talocalcaneal angles in a neutrally aligned and misaligned foot, respectively.
Figure 13B:
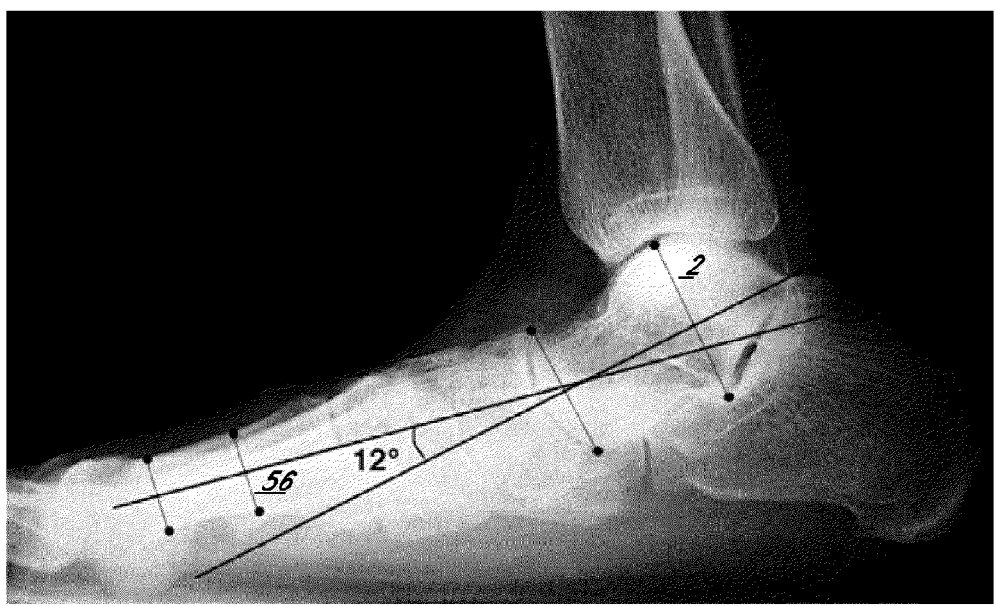
Figure 14A:
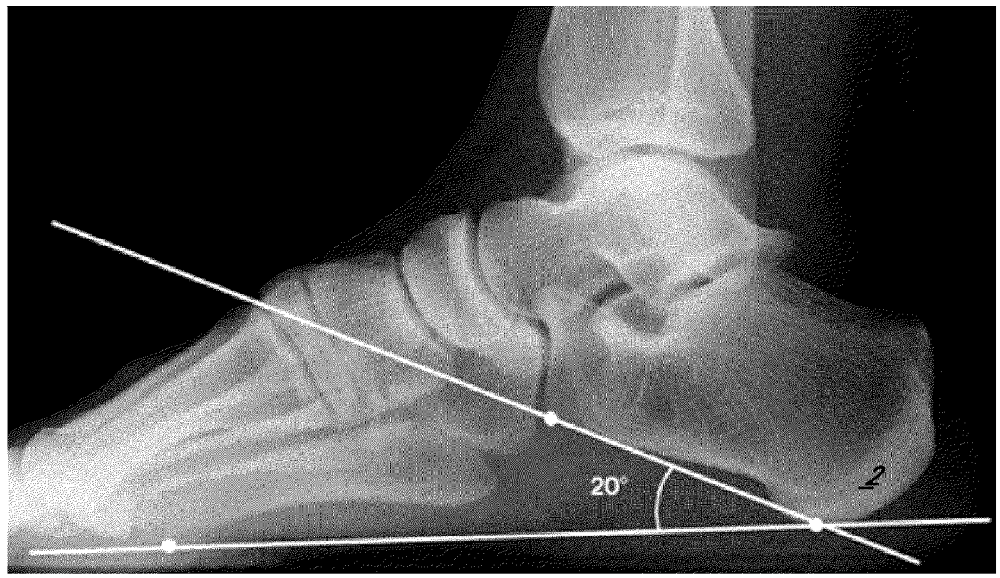
FIGS. 14A and 14B are lateral radiographs of the foot depicting the calcaneal pitch angles in a neutrally aligned and misaligned foot, respectively.
Figure 14B:
Figure 15B:
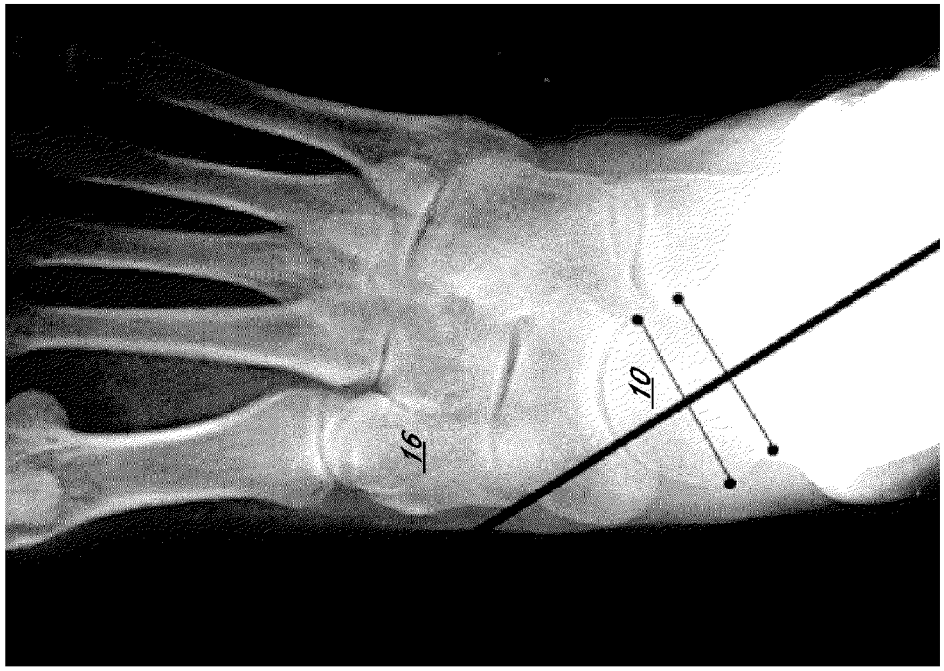
FIGS. 15A and 15B are AP radiographs of the foot depicting AP-talar-first metatarsal angles in a neutrally aligned and misaligned foot, respectively.
Figure 15A:
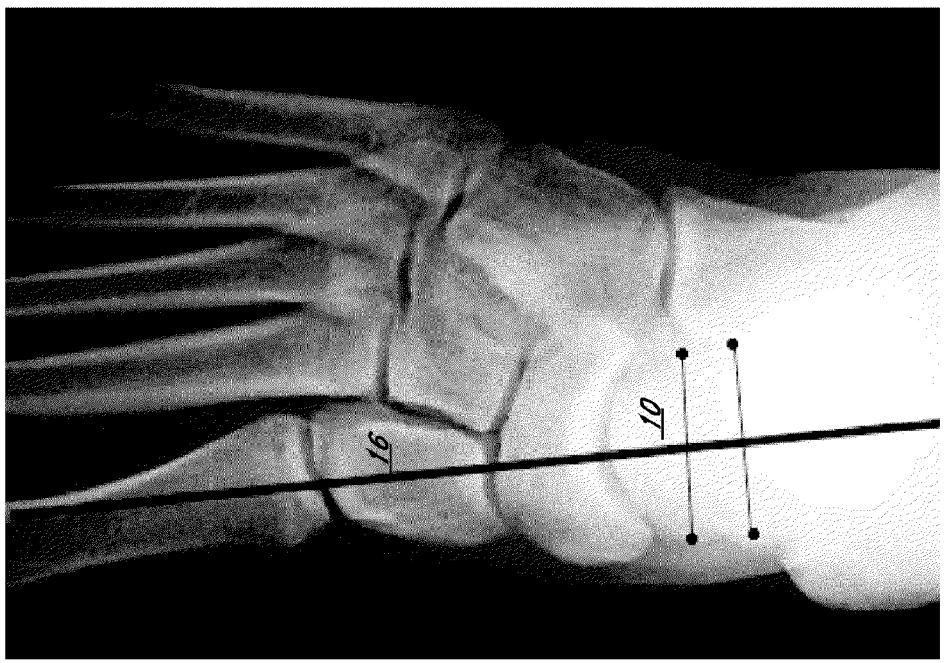
Figure 16A:
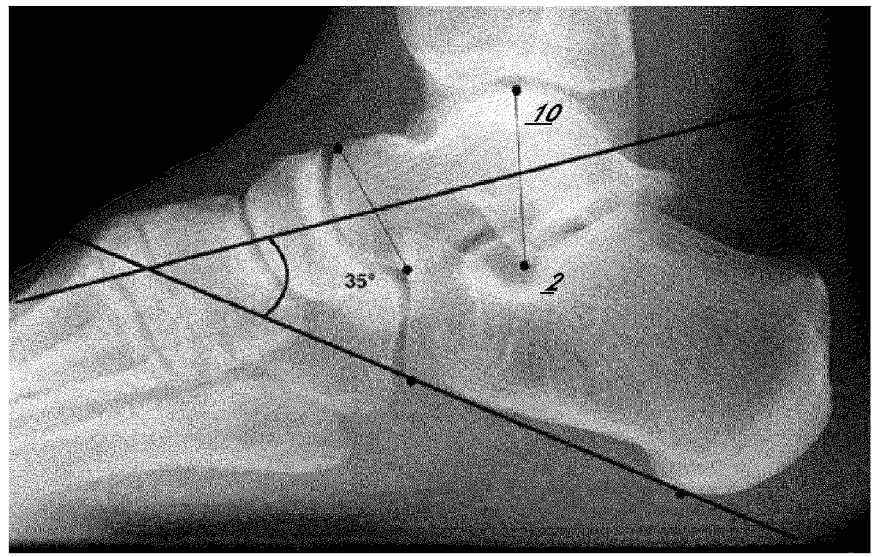
FIGS. 16A and 16B are lateral radiographs of the foot depicting the lateral talocalcaneal angles in a neutrally aligned and misaligned foot, respectively.
Figure 16B:
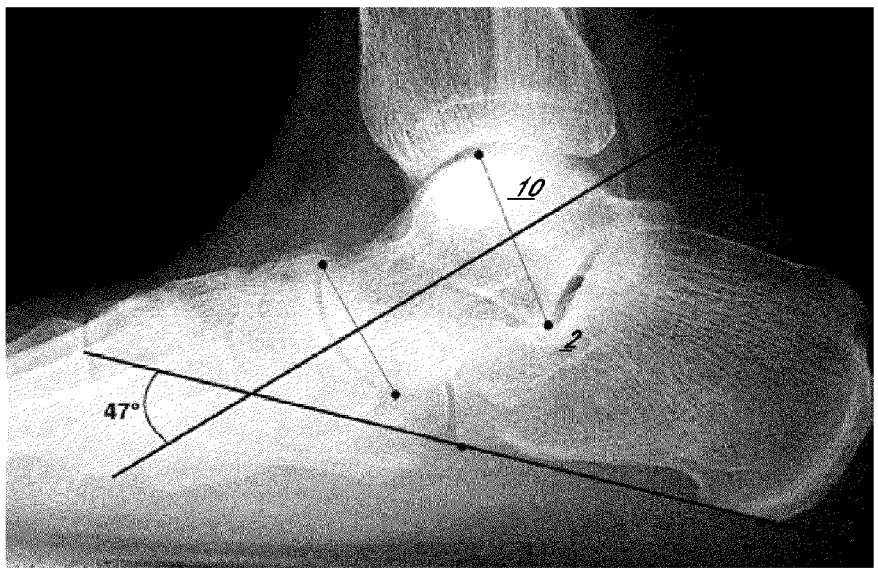
Figure 17B:
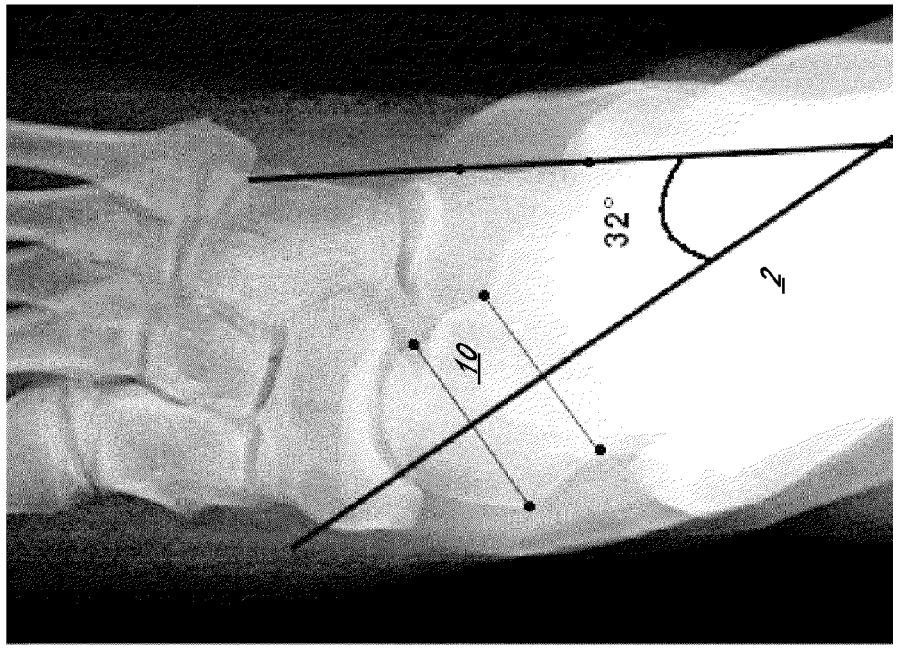
FIGS. 17A and 17B are AP radiographs of the foot depicting AP talocalcaneal angles in a neutrally aligned and misaligned foot, respectively.
Figure 17A:
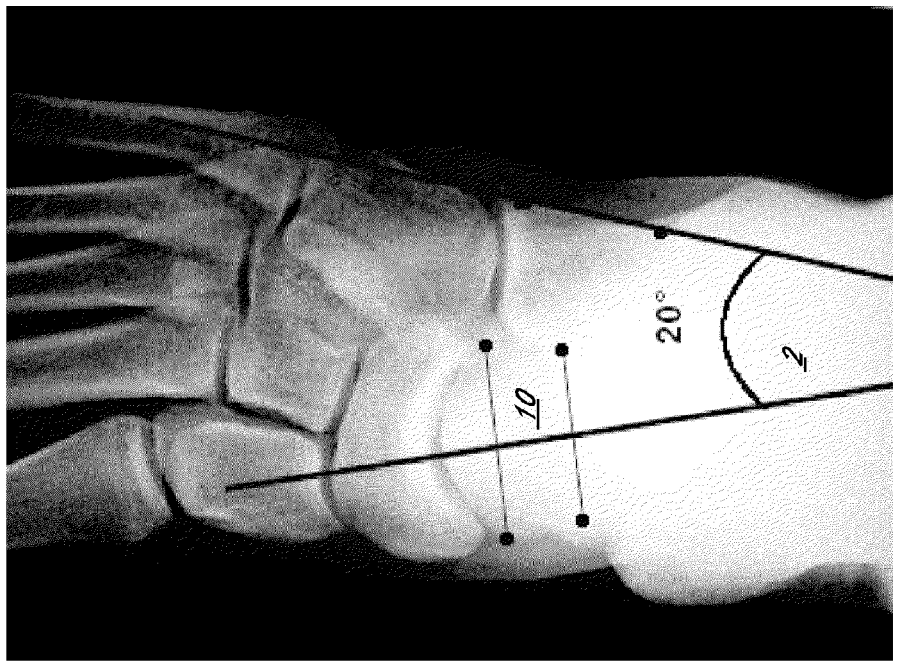

Other radiographic methods of assessing foot alignment are also available. FIGS. 12A and 12B depict the evaluation of talonavicular uncoverage. Talonavicular uncoverage is an indication of forefoot abduction, a component of flatfoot. This measurement is taken from a weight-bearing AP view. This angle represents the degree of shift of navicular 16 on talus 10. Two lines are drawn, one connecting the edges of the articular surface 52 of the talus 10, and one connecting the edges of the articular surface 54 of the navicular 16. The angle formed by these two lines is the talonavicular coverage angle, as seen in FIG. 12A. An angle of greater than 7 degrees indicates lateral talar subluxation, shown in FIG. 12B. A more direct measurement of pes planus, or collapse of the longitudinal arch, is the talar-first metatarsal angle (Meary's angle), shown in FIGS. 13A and 13B. This is an angle formed between the long axis of the talus 2 and first metatarsal 56 on a weight-bearing lateral view. This line is used as a measurement of collapse of the longitudinal arch 50. Collapse may occur at the talonavicular joint, naviculo-cuneiform, or cuneiform-metatarsal joints. In the normal weight-bearing foot, shown in FIG. 13A, the midline axis of the talus 2 is in line with the midline axis of the first metatarsal 56. An angle that is greater than 4° convex downward is considered pes planus. An angle of fifteen to thirty degrees, as in FIG. 13B, is considered moderate flat foot, and an angle greater than 30° is considered severe flat foot. FIGS. 14A and 14B depict radiographs evaluating the calcaneal inclination angle, or calcaneal pitch. A line is drawn from the plantar-most surface of the calcaneus 2 to the inferior border of the distal articular surface. The angle created between this line and the transverse plane, or the line from the plantar surface of the calcaneus 2 to the inferior surface of the fifth metatarsal head, is the calcaneal pitch, shown in FIG. 14A. A decreased calcaneal pitch is consistent with pes planus, as represented in FIG. 14B. There have been differing opinions between researchers concerning the normal range of calcaneal pitch. Eighteen to twenty degrees is generally considered normal, although measurements ranging from seventeen to thirty-two degrees have also been reported to be normal. FIGS. 15A and 15B depict radiographs evaluating the AP-talar-first metatarsal angle. A line drawn through the mid-axis of the talus 10 should be in line with the first metatarsal shaft 56, as in FIG. 15A. If the line is angled medial to the first metatarsal 56 it indicates pes planus, as illustrated in FIG. 15B. FIGS. 16A and 16B depict radiographs evaluating the lateral talocalcaneal angle. The lateral talocalcaneal angle is the angle formed by the intersection of a first line bisecting the talus 10 with a second line along the plantar border or through the long axis of the calcaneus 2. The first line is drawn through two midpoints in talus 10, one at the body and one at the neck. The angle is formed by the intersection of these axes. As shown in FIG. 16A, the normal range is 25-45 degrees. An angle over 45 degrees indicates hindfoot valgus, another component of pes planus, as depicted in FIG. 16B. FIGS. 17A and 17B depict radiographs evaluating the AP talocalcaneal angle, also known as Kite's angle. This is the angle formed by the intersection of a line bisecting the head and neck of talus 10 and a line running parallel with the lateral surface of calcaneus 2. FIG. 17A depicts a foot within the range of normal for adults between 15-30°. Referring to FIG. 17B, an angle greater than 30° indicates hindfoot valgus, another component of pes planus.

Figure 19A:
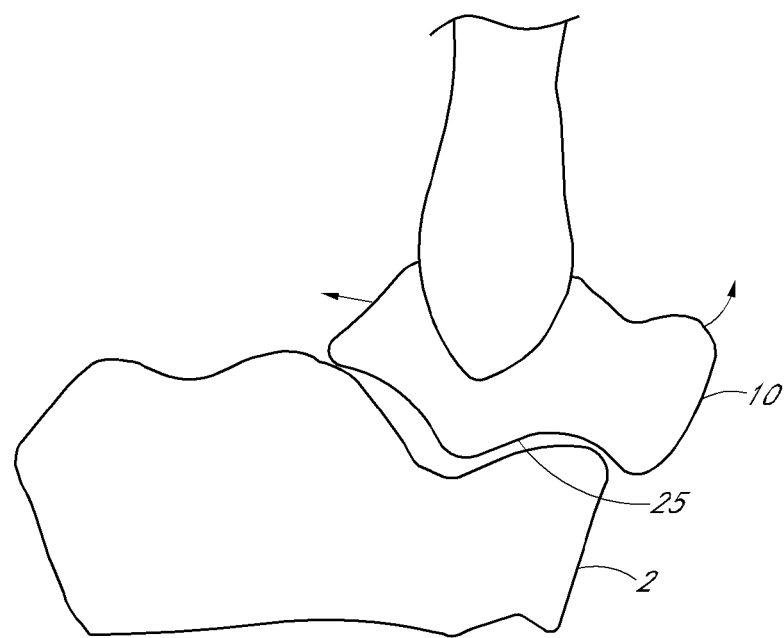
FIGS. 19A and 19B are schematic longitudinal cross-sectional views of the talus and calcaneus in a hyperpronated foot before and after insertion of material into the sinus tarsi.
Figure 19B:
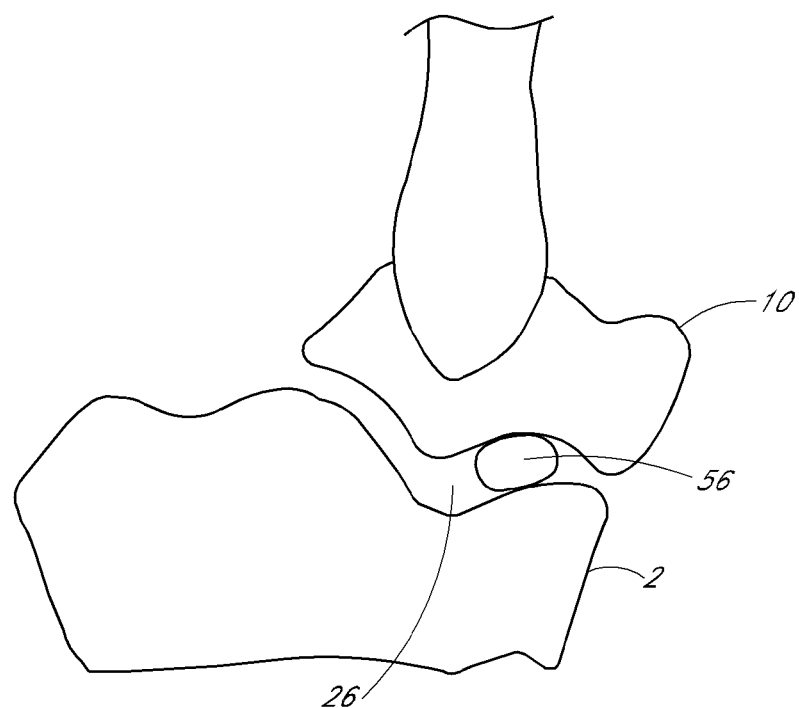

FIGS. 18A and 18B are schematic cross-sectional representations through the sinus tarsi of a neutrally aligned foot compared to a hyperpronated foot, respectively. Due to ligament laxity, the hyperpronated foot has a greater range of motion at talus 10 and calcaneus 2, which causes a shift in load bearing along the medial portion of the foot and tends to flatten the arch. Insertion of material 58 into sinus tarsi 26, alters the range of subtalar motion and limits the range of pronation. FIG. 18C shows that material 58 positioned in sinus tarsi 26 can have a wedge-type effect to position calcaneus 2 to a neutral alignment. FIG. 18D illustrates, however, that over time, the configuration of talus 10 and calcaneus 2 also has a tendency to cause lateral displacement of material 58 through forces exerted onto material inserted into sinus tarsi 26. FIGS. 19A and 19B are schematic longitudinal cross-sectional representations of a hyperpronated foot before and after insertion of material 58 into sinus tarsi 26.

Accordingly, one embodiment of the present invention provides an implant 60 which can be easily located within the tarsal canal, which may or may not deform under post-operative compressive forces, which would ensure that the desired amount of calcaneal eversion has been provided after insertion of the implant 60 and which can be imaged using radiography to determine whether the implant has been properly positioned during the procedure. By placing a device into the tarsal space between talus 10 and calcaneus 2, hindfoot motion and stability may be favorably modified. Such a device may further provide midfoot stability because midfoot-stability is co-dependent on hindfoot stability. Dysfunction of the posterior tibial tendon that supports the foot arch may also be treated by restoring the arch of the foot and relieving the excessive tension on the tendon.

By developing a minimally invasive, catheter-deliverable subtalar implant, disruption of the joint capsule and the ligamentous structures in and around the lateral portion of the foot can be reduced. Current subtalar implants require either transection of the ligaments overlying the sinus tarsi or the dilation of an opening up to about ¾ inch diameter through the ligaments. Dilation of this magnitude will stretch and disrupt the ligaments. In general, the implant in accordance with the present invention may be advanced through a tissue opening of no greater than about 7 mm, and preferably no greater than about 2 mm to about 3 mm.

The development of an inflatable, non-metallic implant will allow the creation of an in-situ customized prosthesis that will also minimize trauma to the surrounding tissue during the implantation procedure and with long-term use. This will considerably shorten the postoperative recuperation period compared to existing devices and reduce postoperative pain and swelling. Moreover, because the integrity of the tissue overlying the sinus tarsi is preserved through minimally invasive implantation, the intact tissue is able to assist in anchoring the implant in the sinus tarsi. By customized, the inventor contemplates an implant that is at least partially conformable to the anatomical cavity in which it resides, at least prior to any polymerization or other curing step.

Figure 20A:
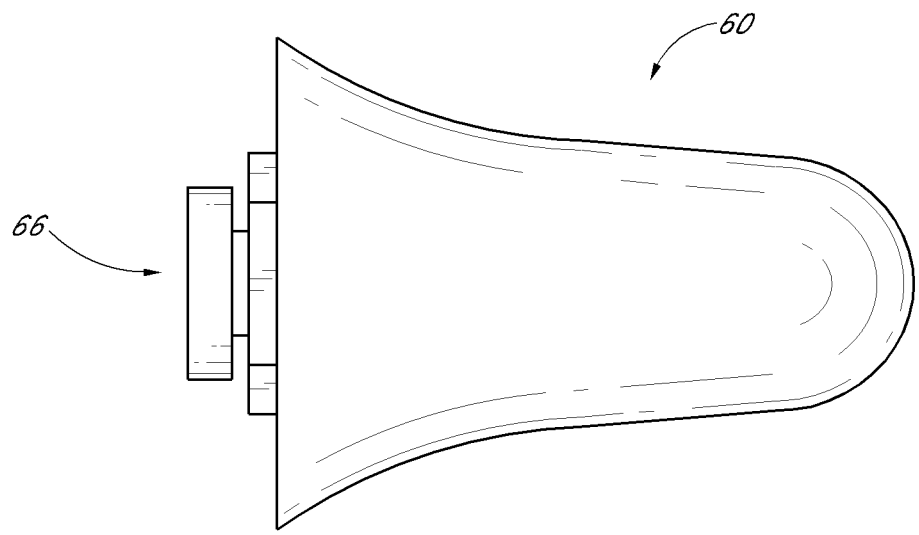
FIGS. 20A and 20B are side elevation and cross-sectional views of one embodiment of the implant.
Figure 20B:
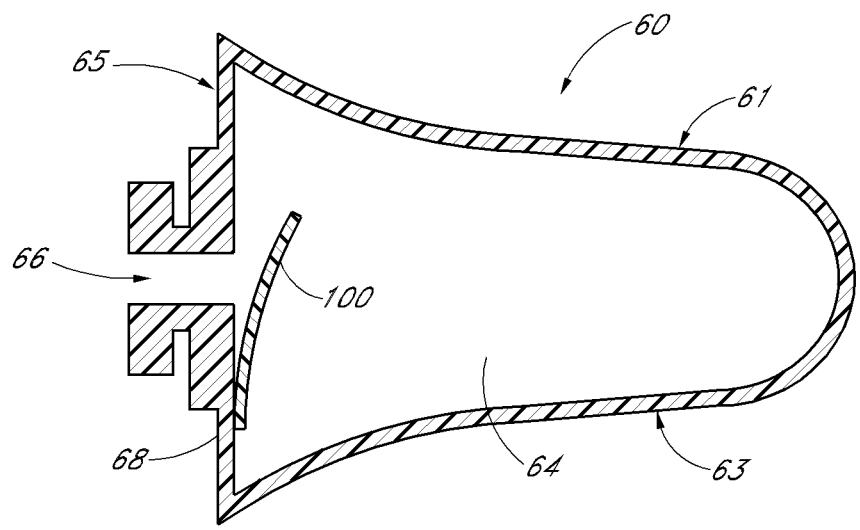

In one embodiment of the invention, illustrated in FIGS. 20A and 20B, the implant 60 comprises an inflatable compartment 64 and an inflation port 66. Inflation port 66 provides access to compartment 64 without compromising the integrity of compartment 64 and causing leakage. In one embodiment of the invention, implant 60 will form a custom shape that approximates the shape of sinus tarsi 26. The custom shape is defined on its superior-medial surface 61 by the inferior surface of talus 10, on its inferior-medial surface 63 by the superior surface of calcaneus 2, and on its lateral surface 65 by soft tissue structures including the fascia. It is preferred, but not required, that the shape have a large lateral surface area 68. A large lateral surface takes advantage of the intact ligaments and soft tissue along the lateral border of sinus tarsi 26 to hold implant 60 in place. The implant has a lateral surface area 68 of between about 2 square centimeters to about 5 square centimeters, preferably between about 3 square centimeters to about 4 square centimeters, and more preferably about 3.8 square centimeters. A custom-shaped implant 60 is also better adapted to affect the highly variable anatomy of the subtalar joint and to alter the highly variable geometry and motion of the joint. A custom-shaped implant can be configured to have a greater contact surface area with sinus tarsi 26 and can disperse the loading of the subtalar joint across a greater surface area compared to non-customized implants. The size and shape of sinus tarsi 26 is also varies with foot position. Therefore, the surgeon will position the foot during the procedure based upon the anatomy of a particular patient and the characteristics of the selected implant. One embodiment of the implantation procedure is described in detail below.

Generally, the area of the lateral-proximal surface 68 of the implant will be at least about twice the cross-sectional area of the dilated tissue access tract. Often, the lateral surface area will be at least 5×, 8×, 10× or 20× or more than the access tract to resist migration of the implant.

In another embodiment, the implant is semi-customizable. The surgeon is able to limit certain dimensions or features of the semi-customizable implant by selecting a balloon having a shorter length, diameter and/or volume. The implant shape is further adjusted by allowing a variable degree of inflation. Variable inflation may allow deeper positioning of the implant within the sinus tarsi by providing implant 60 with a smaller diameter for deeper insertion into the narrow tarsal canal.

Figure 21A:
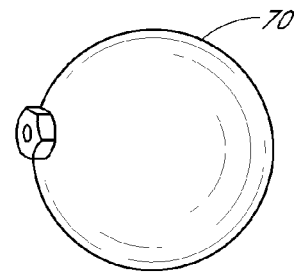
FIGS. 21A through 21H depict side elevation views of various embodiments of non-conforming implants.
Figure 21E:
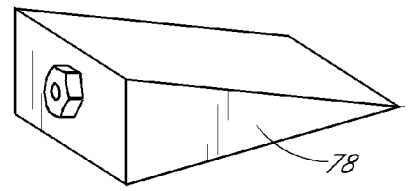
Figure 21B:
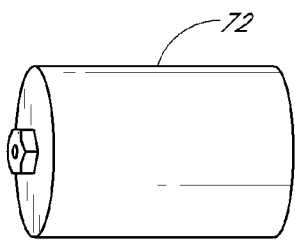
Figure 21F:
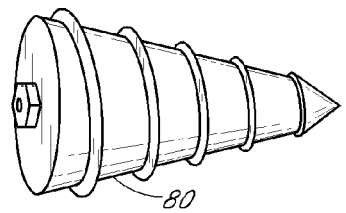
Figure 21C:
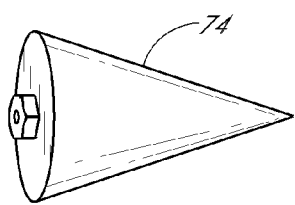
Figure 21G:
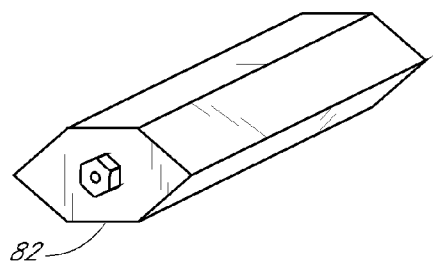
Figure 21D:
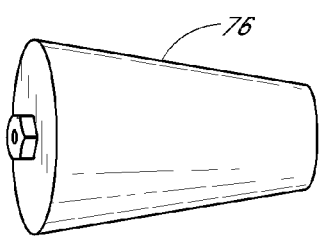
Figure 21H:
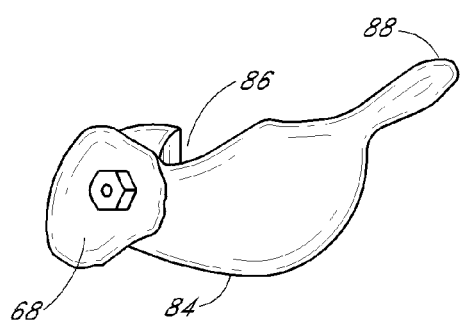

In still another embodiment, the implant shape is preselected by the surgeon. The implant is compressible onto a catheter for minimally invasive delivery, but assumes a preconfigured shape with inflation. A preconfigured shape may be advantageously used to force a particular foot alignment or to facilitate anchoring of the implant. One indication for this implant and procedure is the hyperpronated, flexible and reducible flatfoot. The most common patient with this indication is pediatric, but adults with posterior tibial tendon dysfunction or hyper-pronation in the absence of subtalar joint and mid tarsal joint arthritis are also eligible. FIGS. 21A through 21H represent implants of various possible shapes for nonconforming implants. The implant can be spherical 70, cylindrical 72, conical 74, frusta-conical 76, wedge-shaped 78, helical 80, polyhedral 82 or any three-dimensional shape 84 capable of positioning in the sinus tarsi. FIG. 21H is one embodiment of implant 60 advantageously fitted to the sinus tarsi 26 of a left foot. The implant, when inflated, may include a groove 86 or cavity dimensioned for fitting around the cervical ligament 40 and a distal tip 88 for anchoring implant 60 in a narrowing of the sinus tarsi 26 along the interosseous ligament 38. A large lateral surface area 68 uses the soft tissue at the lateral opening of the sinus tarsi 26 to maintain the desired position of the implant. This implant has a length of about fifteen millimeters to about twenty millimeters, a lateral diameter of about ten to about fifteen millimeters and a medial diameter of about six to about eight millimeters.

Figure 22A:
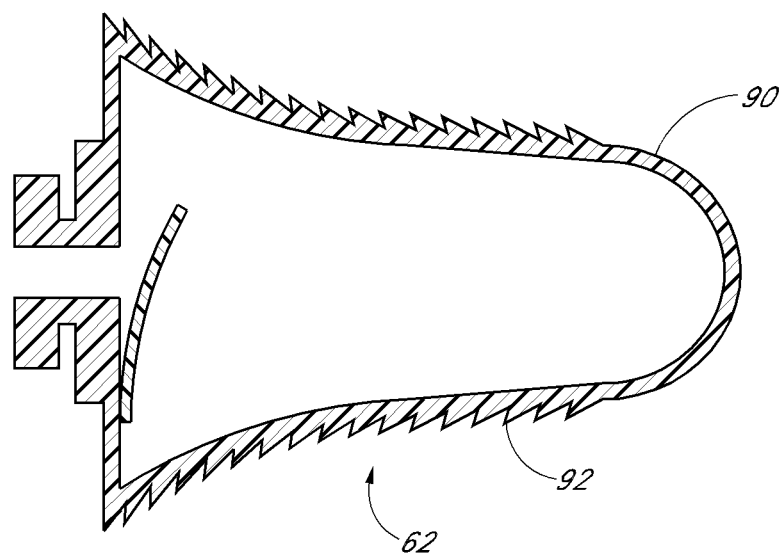
FIGS. 22A and 22B are elevation and cross sectional views of one embodiment of the invention having a ridged outer surface.
Figure 22B:
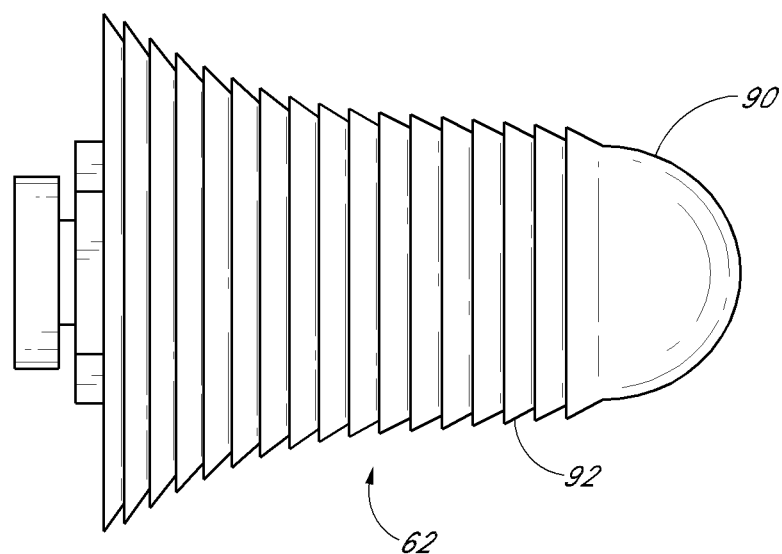

The outer surface 90 of implant 60 may be smooth, textured or comprise any of a variety of protrusions or indentations to reduce the risk of implant migration. FIGS. 22A and 22B show one embodiment of the invention with a plurality of ridges 92 on the outer surface. Texturing on the outer surface 90 of implant 60 may provide an interference fit or increased friction between implant 60 and sinus tarsi 26 to resist displacement of implant 60 from its desired position. In a further embodiment, the outer surface 90 may further comprise cellular ingrowth regions that allow ingrowth of the surrounding tissue and further resist displacement of the implant. The pore size of the cellular ingrowth regions may range from about 20 µm to about 100 µm or greater. Desirably, the porosity of the cellular ingrowth regions ranges from 20 µm to 50 µm and, in many embodiments, the porosity of the cellular ingrowth regions ranges from 20 µm to 30 µm.

If more aggressive anchoring of the implant is desired, the inflatable member may be further configured to facilitate attachment of implant 60 to soft tissue or bone. In one embodiment, sutures, clips, staples, tacks, pins, hooks, barbs, or other securing structures that can at least partially penetrate the surrounding tissue or bone are used. These securing structures may be made from a variety of materials, including metals, polymers, ceramics or absorbable materials. Absorbable materials include but are not limited to polylactic acid (PLA) or copolymers of PLA and glycolic acid, or polymers of p-dioxanone and 1,4-dioxepan-2-one. A variety of absorbable polyesters of hydroxycarboxylic acids may be used, such as polylactide, polyglycolide and copolymers of lactide and glycolide, as described in U.S. Pat. Nos. 3,636,956 and 3,297,033, which are hereby incorporated in their entirety herein by reference. The use of absorbable materials allows the securing structure to dissolve or resorb into human tissue after a known or establishable time range, from a week to over a year.

Figure 23A:
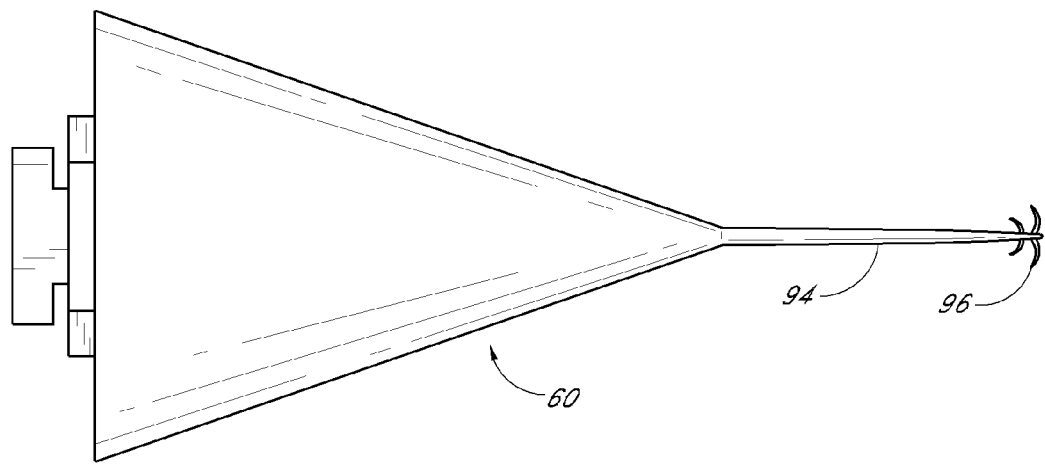
FIGS. 23A and 23B are cross-sectional views of the foot with various embodiments of barbs for anchoring the implant.
Figure 23B:
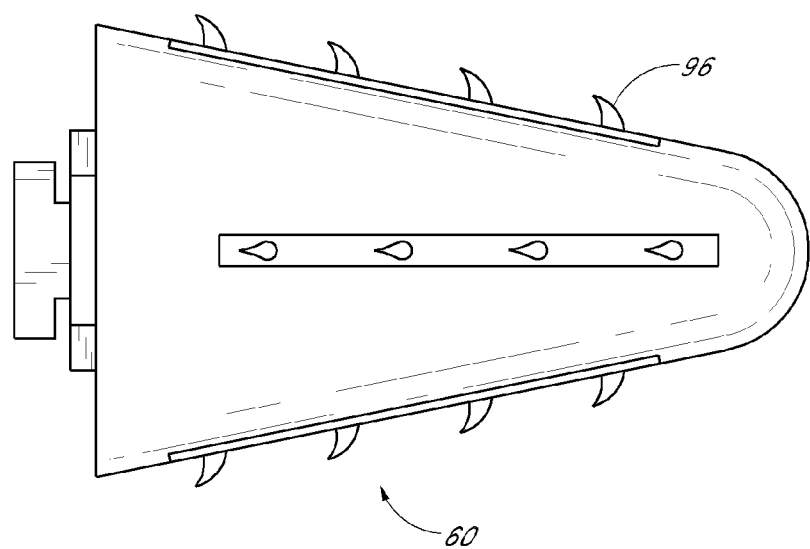

In one non-limiting example, shown in FIG. 23A, a distal anchor 94 with at least two or three or four or more barbs 96 is attached to the medial surface 98 of implant 60 for anchoring at the medial portion of the sinus tarsi 26. In another non-limiting example in FIG. 23B, one or more short pointed barbs 96 are integrally formed with implant 60 or secured thereto using any of a variety of attachment techniques which are suitable depending upon the composition of implant 60. As the implant is inserted into sinus tarsi 26, barbs 96 penetrate the surrounding soft tissue, bone or ligaments. Hooks may also be attached to or integrally formed with implant, so that the implant can be hooked into the surrounding tissue, possibly in combination with the use of a bioadhesive. Such hooks and barbs may be formed from a bioabsorbable or dissolvable material as has discussed above.

In one embodiment of the invention, implant 60 comprises any of a variety of flexible materials that resist stretching. These materials include but are not limited to polyethylene, polyolefins, polyvinyl chloride, polyester, polyimide, polyethylene terephthalate (PET), polyamides, nylon, polyurethane and other polymeric materials. One skilled in the art can select the material based upon the desired compliance, biocompatability, rated burst pressure and other desired characteristics. In one embodiment, the inflatable member has a wall thickness of about 0.001 cm to about 0.05 cm. In another embodiment, the inflatable member has a thickness of about 0.02 cm to about 0.03 cm. Generally, the inflatable member has a rated burst pressure of greater than 60 atmospheres (ATM) for resisting bursting and extrusion of inflation material under physiologic loading. In another embodiment, the inflatable member has a rated burst pressure of at least about eight ATM or more. A lower burst pressure can be used where a curable material is used to inflate the inflatable member and will bear the loading of the subtalar joint. In a further embodiment of the invention, implant 60 is integrally formed with deformable wire supports within the material used to form the inflatable member. One possible function of the wire support to provide some stiffness to the implant during the insertion process to allow the operator to insert the implant into distal sulci or crevices of the sinus tarsi. A wire support can also comprise a shape memory metal, such as nitinol. Upon insertion of the implant into the sinus tarsi, the body heat of the patient will cause the wire support to change shape and expand to the borders of the sinus tarsi. Those skilled in the art understand that any of a variety of biocompatible, deformable metals may be used to form the skeleton.

In addition to providing access to inflate the inflatable compartment, the inflation port may comprise other features to facilitate use of the implant. The inflation port may be self-sealing or have a one-way valve to obviate the need for a separate sealing of the implant after inflation. Valve configurations include but not limited to hemostatic-type valves, flap valves or duckbill valves. In some embodiments, a pierceable septum may be used. A flap valve 100 is shown in FIG. 20B. The flapper portion of the valve can be formed from silicone, rubber, neoprene or any other flexible material known to those with skill in the art. Less flexible materials may be used for the valve where the inflation fluid is highly viscous or curable. One skilled in the art can select the type of seal based upon the inflation pressures of the implant, the viscosity of the inflation fluid, curability and other characteristics. Inflation port 66 may be further configured to minimize any leakage of material from either implant 60 or the delivery system during the detachment process. Inflation port 66 may include radio-opaque markers to allow a clinician to later deflate or adjust implant 60 transcutaneously with a hypodermic needle.

The material used to inflate inflatable compartment 62 includes any of a variety of biocompatible materials, including but not limited to saline, silicone polymers, polyurethane polymers, linear or branched polyols, PMMA or others known in the art. Solid materials, such as small polymeric metallic microspheres, microtubules or microdiscs can also be used as a filling agent. The material can also be a combination of materials, such a curable liquid substrate and a catalyst, that can solidify within implant 60. Several U.S. patents disclose various types of polymers or proteins that, assertedly, can be injected into a joint as a liquid or semi-liquid composition that subsequently harden into a solidified material. For example, U.S. Pat. No. 5,556,429 (Felt 1996), herein incorporated by reference, discloses injection of a fluidized mixture of a biocompatible polymer (such as a silicone or polyurethane polymer) and a biocompatible "hydrogel" (a hydrophilic polymer, formed by steps such as using an agent such as ethylene dimethacrylate to cross-link a monomer containing a hydroxyalkyl acrylate or methacrylate), into a space. After injection, the polymer and hydrogel mixture can be set into solidified form by means such as ultraviolet radiation, which can be introduced into the space by a fiber optic device. Other articles on surgically implantable polymers is contained in numerous published items; recent review articles include Peppas et al 1994, Hubbell 1995, Stokes 1995, Burg et al 1997, Lewis 1997, Kim and Mooney 1998, and Ambrosio et al 1998, herein incorporated by reference. Other discussions of biocompatible implantable materials are also available in various textbooks, such as Silver 1994, herein incorporated by reference. Other combinations of inflation materials may include the addition of iodine, barium or other radio-opaque component. One skilled in the art can select the desired material based upon the viscosity, density, cure time, degree of exothermic cure reaction, radio-opacity and other characteristics. For curable materials, one skilled in the art may consider the load-bearing strength, tensile strength, shear strength, fatigue, impact absorption, wear characteristics and other factors of the cured material.

Figure 24A:
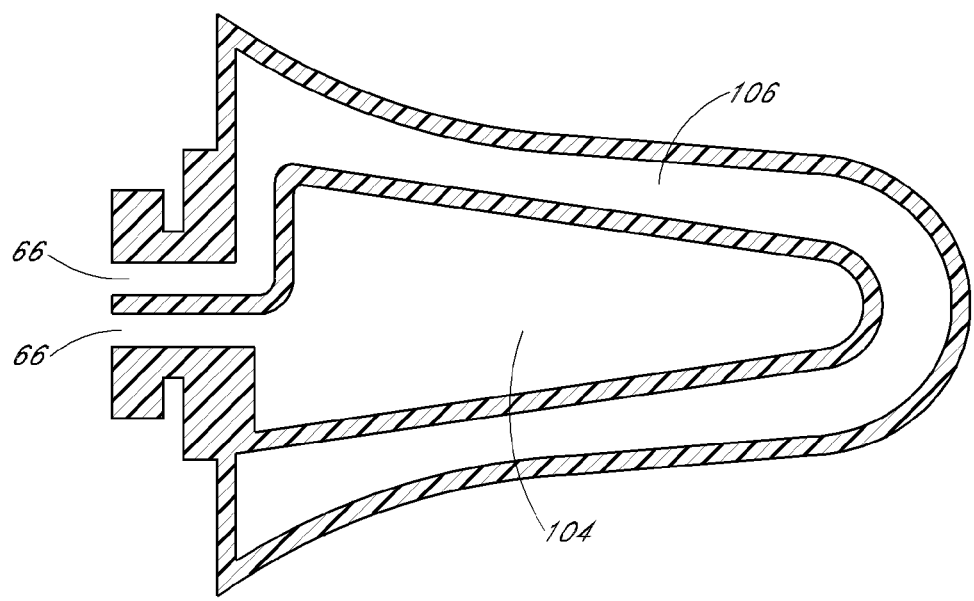
FIGS. 24A and 24B represent various embodiments of the invention comprising multiple inflatable compartments.
Figure 24B:
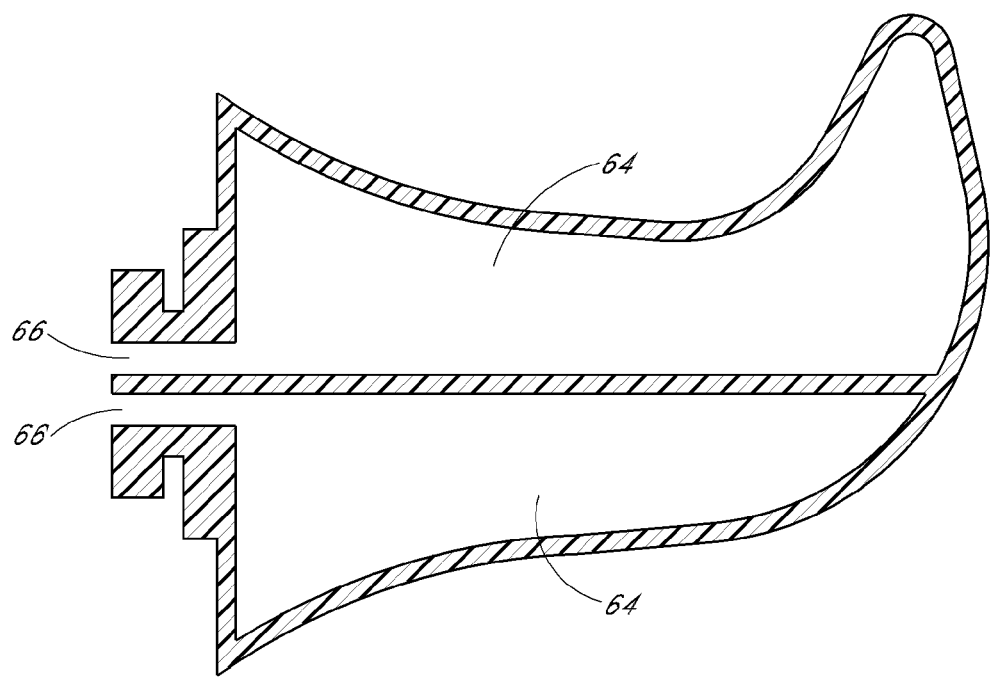

In another embodiment, implant 60 has multiple inflation ports and multiple compartments such that different portions of implant 60 can be independently inflated. FIGS. 24A and 24B are non-limiting examples of two-compartment inflatable members. The delivery catheter for an implant comprising multiple compartments may have multiple fluid ports to allow independent inflation of the compartments. Different compartments may be inflated with different materials having different characteristics. In one embodiment of the invention, implant 60 has an inner compartment 104 and an outer compartment 106. Outer compartment 106 may be inflated with a curable material to provide a solid material at the surface of implant 60. Inner compartment 104 may be inflated with a liquid material to provide limited deformability to implant 60. Alternatively, outer compartment 106 may be inflated with a liquid material and inner compartment 104 is inflated with a curable material. This particular embodiment may provide cushioning to the joint surfaces by providing a compressible implant surface, yet the curable core provides some resilience to complete compression.

Implant 60 further comprises a coupling interface 108 that releasably attaches implant 60 to the delivery system. Coupling interface 108 is generally located on or about inflation port 66 and allows for inflation of implant 60 through the delivery system without leakage of material into the surrounding tissue. Coupling interface 108 also allows transmission of force, including torque, from the delivery system to the implant to facilitate positioning of implant 60. Coupling interface 108 is configured to allow detachment of implant 60 from the delivery system and, optionally reattachment of the delivery system.

Figure 25A:
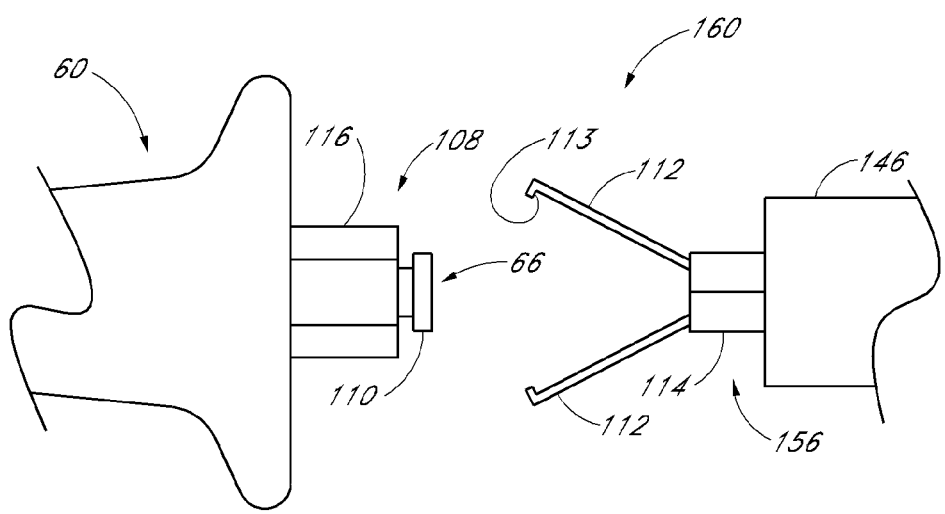
FIGS. 25A and 25B are elevation views of one embodiment of the coupling interface and the distal end of a complementary delivery catheter.
Figure 25B:
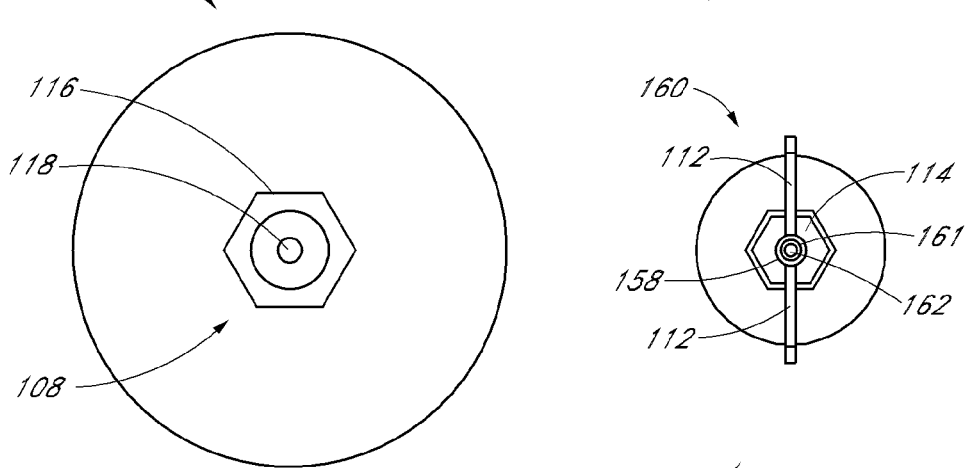
Figure 25C:
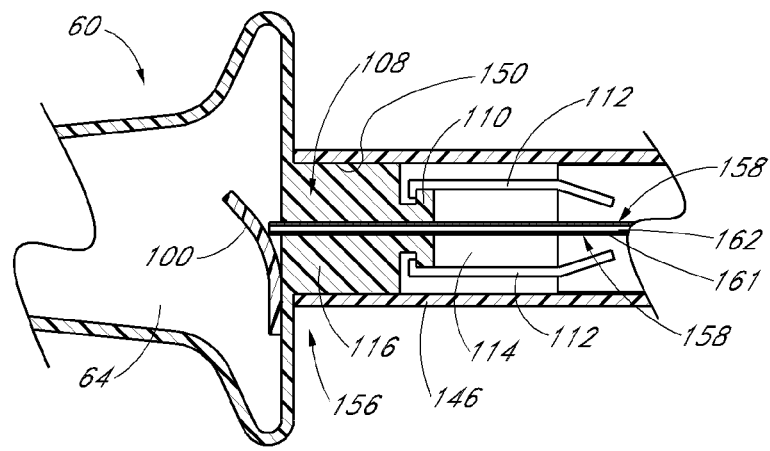
FIG. 25C is a cross-sectional view of the implant in FIGS. 25A and 25B attached to a delivery catheter.
Figure 26A:
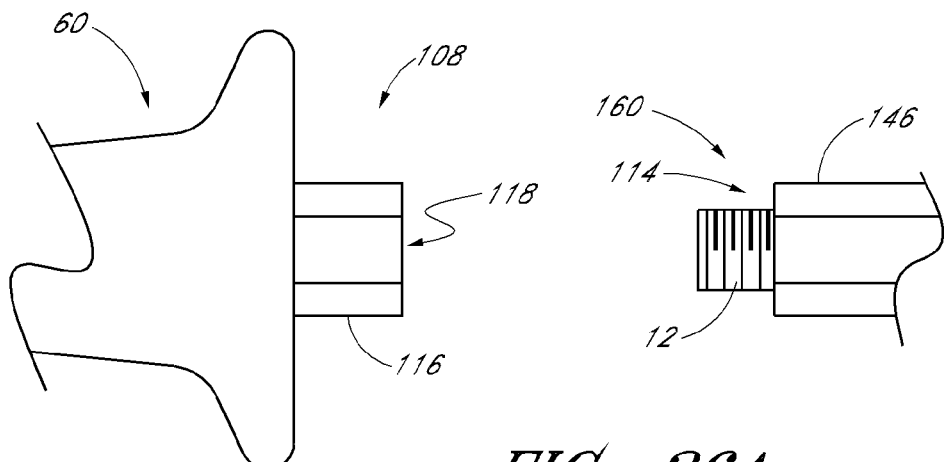
FIGS. 26A and 26B are elevation views of another embodiment of the coupling interface and the distal end of a complementary delivery catheter.
Figure 26B:
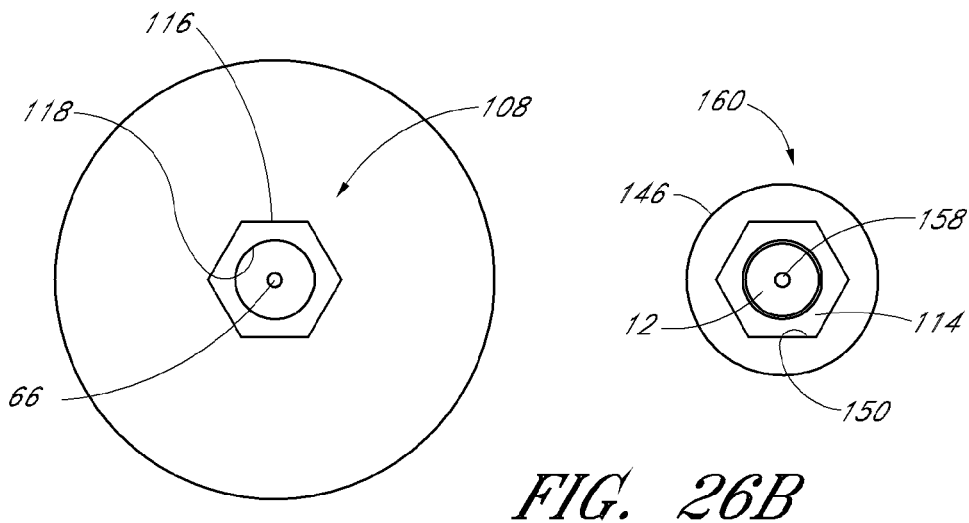
Figure 26C:
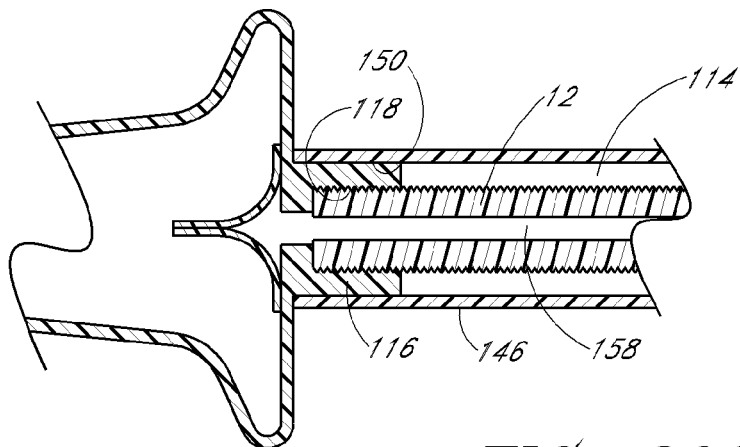
FIG. 26C is a cross-sectional view of the implant in FIGS. 26A and 26B attached to a delivery catheter.

FIGS. 25A through 25C illustrate one embodiment of the invention, where coupling interface 108 comprises a flange 110 surrounding inflation port 66. Flange 110 is capable of being grasped by prongs 112 extending from the delivery catheter 114. Coupling interface 108 further comprises a base 116 having a polygonal or otherwise rotationally keyed cross-section. Base 116 may be positioned between coupling interface 108 and inflatable compartment 64 and is capable of forming another mechanical interfit with an outer sheath 146 over catheter 114. This additional mechanical interfit provides further resistance to dislodging or separation of implant 60 from delivery catheter 114 during implantation, especially from rotational forces. FIGS. 26A through 26C depict another embodiment of coupling interface 108, comprising base 116 and an internal threaded lumen 118 for accepting a threaded core 120 extending from the delivery catheter 114. The attachment of coupling interface 108 to delivery catheter 114 is described in further detail below.

Figure 27C:
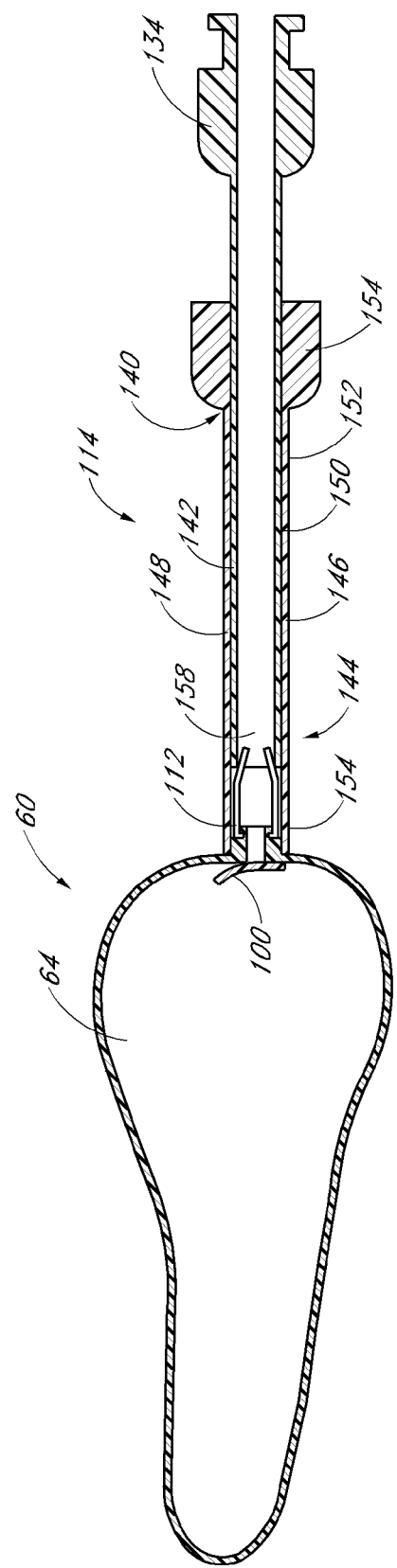

One embodiment of the delivery system is illustrated in FIGS. 27A through 27C, comprising a cannula or sheath 122, a sizing catheter 124 with an inflatable balloon tip 126 and delivery catheter 114 attachable to implant 60. Cannula 122 is made from plastic with radio-opaque markers to allow imaging of the cannula. Cannula 122 can be introduced into the sinus tarsi over a needle 130. Cannula 122 has a length of about two inches to about six inches and a diameter of about 12 gauge to about 18 gauge. A lumen 128 is provided in cannula 122 to allow passage of sizing catheter 124 and delivery catheter 114 with attached implant 60. Alternatively, the cannula can be made of metal and has a distal tip sufficiently sharp to pierce the skin, connective tissue and ligaments overlying the sinus tarsi. A metal cannula with a sharp tip would not require insertion of the cannula over a needle or guidewire.

Sizing catheter 124, shown in FIG. 27B, has a length of about two inches to about eight inches and a diameter capable of passing through cannula 122. Sizing catheter 124 has radiographic markers for determining its position in the foot during radiographic imaging. The proximal end 132 of sizing catheter 124 comprises a Luer fitting 134 or other similar type of mechanical lock for attaching a syringe 136. A lumen 138 within the sizing catheter 124 provides a conduit from syringe 136 to sizing balloon tip 126 at the distal end of sizing catheter 124. Sizing balloon tip 126 has a length of about fifteen millimeters and a diameter of about six to about twelve millimeters. Sizing balloon tip 126 can have any of a variety of shapes similar to those described for implant 60. Syringe 136 has markings so that the volume of fluid inflated into sizing balloon tip 126 can be measured quantitatively. Sizing catheter 124 is capable of performing a number of functions. Insertion of sizing catheter 124 through cannula 122 initiates the dilatation of sinus tarsi 26 and helps to prepare the path for introduction of permanent implant 60. By filling sizing catheter balloon 126, the surgeon is able to determine the volume of non-compressible fluid required to fill sinus tarsi 26 to the proper degree necessary for selection of the configuration of permanent implant 60 capable of controlling pronation within the proper range.

Figure 28A:
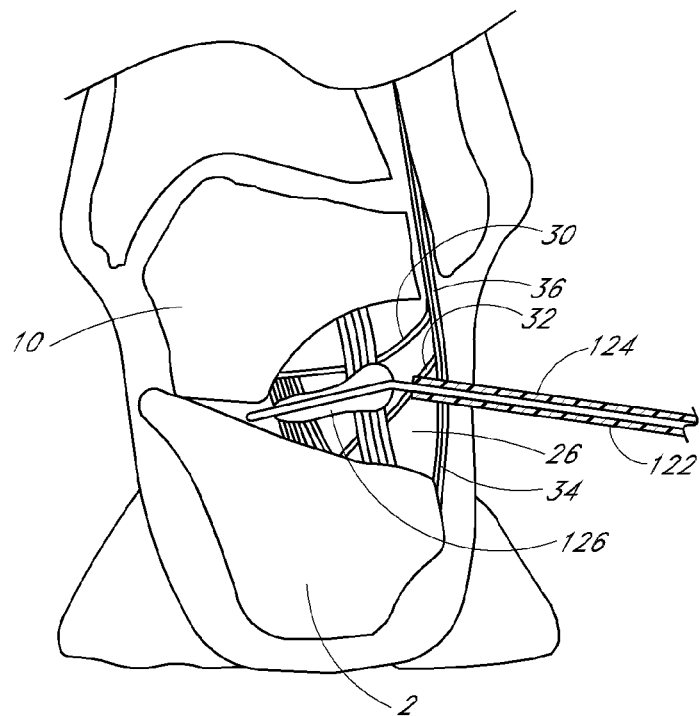
FIGS. 28A and 28B are schematic cross-sectional views of the foot before and after inflation of the sizing catheter.

Alternatively, sizing balloon 126 may comprise a high-compliance material that is capable of conforming to the surrounding anatomical structures. By filling sizing balloon 126 with a radio-opaque fluid under fluoroscopy or with radiography, the surgeon can determine the proper three-dimensional shape and of the cavity 26. An implant 60 can be selected to correspond with the predetermined shape and/or size. FIG. 28A is a cross-sectional schematic of high-compliance sizing balloon 126 inflated in sinus tarsi 26. As the balloon 126 is inflated in FIG. 28B, loose ligaments and connective tissue will be displaced while balloon 126 conforms around taut structures. This shape information permits selection or construction of an implant having a predetermined shape or determination of the need for a semi-customizable or fully customizable implant.

In an alternative embodiment of the delivery system, sizing catheter 124 is omitted because the inflation characteristics of the implant allow implant 60 to be adapted to structural variations of the anatomy. Selection of a particular size or shape of implant is not required in this alternative embodiment. In this embodiment, the surgeon can partially inflate the implant, evaluate the effect on the foot alignment and flexibility, and continue to inflate, deflate and/or position the implant until a desired result is achieved. The delivery catheter 114 may then be detached and withdrawn, leaving the implant 60 in place.

FIG. 27C shows one embodiment of delivery catheter 114, comprising a proximal end 140, a body 142, a distal end 144 and an outer sheath 146. The delivery catheter has a length of about two inches to about ten inches and has a diameter capable of passing through cannula 122. Catheter 114 may contain radiographic markers for determining its position in the foot with imaging. Proximal end 140 of delivery catheter 114 comprises at least one Luer fitting 134 or other similar type of mechanical lock for attaching a syringe to inflate the implant with material. Body 142 of delivery catheter 114 comprises at least one lumen 148 to provide a conduit from the syringe or other source to implant 60 fastened to distal end 144 of delivery catheter 114. A multi-lumen catheter may be used where the implant has multiple compartments, or where multiple reactive materials are used to inflate the implant. The use of multiple lumens may prevent reactive components of the implant material from reacting within the catheter and prevent clogging of the catheter. For inflation materials that use ultra-violet light for curing, a fiber-optic line can be inserted through the lumen 148 to provide the ultra-violet light. Outer sheath 146 comprises an inner surface 150, an outer surface 152, a proximal portion 154 and a distal portion 156. Outer sheath 146 also has a retracted position that exposes the distal end 144 of delivery catheter 114 and an extended position that covers distal end 144 of delivery catheter 114.

Distal end 144 of delivery catheter 114 comprises an inflation lumen 158 and a coupler for attaching to coupling interface 108 of implant 60. In the embodiment of the invention seen in FIG. 25A, where coupling interface 108 comprises flange 110, the coupler 160 of delivery catheter 114 comprises a plurality of radially outward-biased graspers or prongs 112 extending distally. Graspers 112 may comprise bent wires, thin arcuate sheets, or any other configuration known to those with skill in the art that is capable of engaging flange 110 and applying a proximally directed force to flange 110. Referring back to FIG. 27C, when outer sheath 146 of delivery catheter 114 is in the extended position, inner surface 150 of outer sheath 146 will contact prongs 112 and apply radially inward forces against prongs 112. These forces move the prongs 112 closer together and allow the prongs 112 to engage the edge of flange 110 on implant 60.

If outer sheath 146 is further extended, inner surface 150 of sheath 146 will contact base 116 of coupling interface 108. Base 116 of implant 60 has a polygonal cross-section capable of forming a mechanical interfit with a polygonal cross-section of inner surface 150 of outer sheath 146. Distal portion 156 of sheath 146 will also exert a distally directed counter-force on implant 60 in opposition to the proximally directed force on the implant from the prongs 112 to firmly attach implant 60 to the delivery catheter 114. If sheath 146 is retracted, the mechanical interfit with base 116 is relieved and radially inward forces on prongs 112 are removed. Prongs 112 will resume their outward bias and distract from flange 110 of implant 60, causing release of implant 60. As previously mentioned, delivery catheter 114 shown in FIG. 26C, may alternatively comprise a slideable inner core 161 within the inflation lumen 158 of delivery catheter 114 that is capable of extending through coupling interface 108 to engage inflation port 66 of implant 60. A lumen 162 in inner core 161 provides a conduit to inflate attached implant 60 with material.

In the embodiment of implant 60 shown in FIG. 26A, where coupling interface 108 comprises a threaded lumen 118, the delivery catheter 114 comprises an outer sheath similar to the sheath described above. The inner core of this embodiment of the delivery catheter, however, comprises a lumen 166 and a threaded outer surface 168 complementary to threaded lumen 118 of implant 60. Implant 60 attaches to delivery catheter 114 by rotating inner core 120 into threaded lumen 118 of the implant. To resist rotation of implant 60 from frictional forces during the attachment or detachment of implant 60, the polygonal cross-section of inner surface 150 of outer sheath 146 is capable of forming a mechanical interfit with the polygonal cross-section of coupling base 116 on implant 60 when outer sheath 146 is extended.

In an alternative embodiment of the delivery system, a guidewire or guide pin having a diameter of about 0.010 inch to about 0.038 inch and a length of about four inches to about eight inches is provided for insertion into the sinus tarsi. The guidewire is insertable through a needle inserted into the sinus tarsi. The needle is withdrawn after the guidewire is positioned. An introducer may be passed to further dilate the passage to the sinus tarsi. The sizing and delivery catheters are adapted for passage over the guidewire into the sinus tarsi. In this embodiment, both catheters would each have at least two lumens. One lumen is used to pass the catheter over the guidewire and the other lumen would be used to inflate the sizing balloon or implant. These lumens may be oriented in a dual concentric configuration or adjacent to each other.

Figure 29:
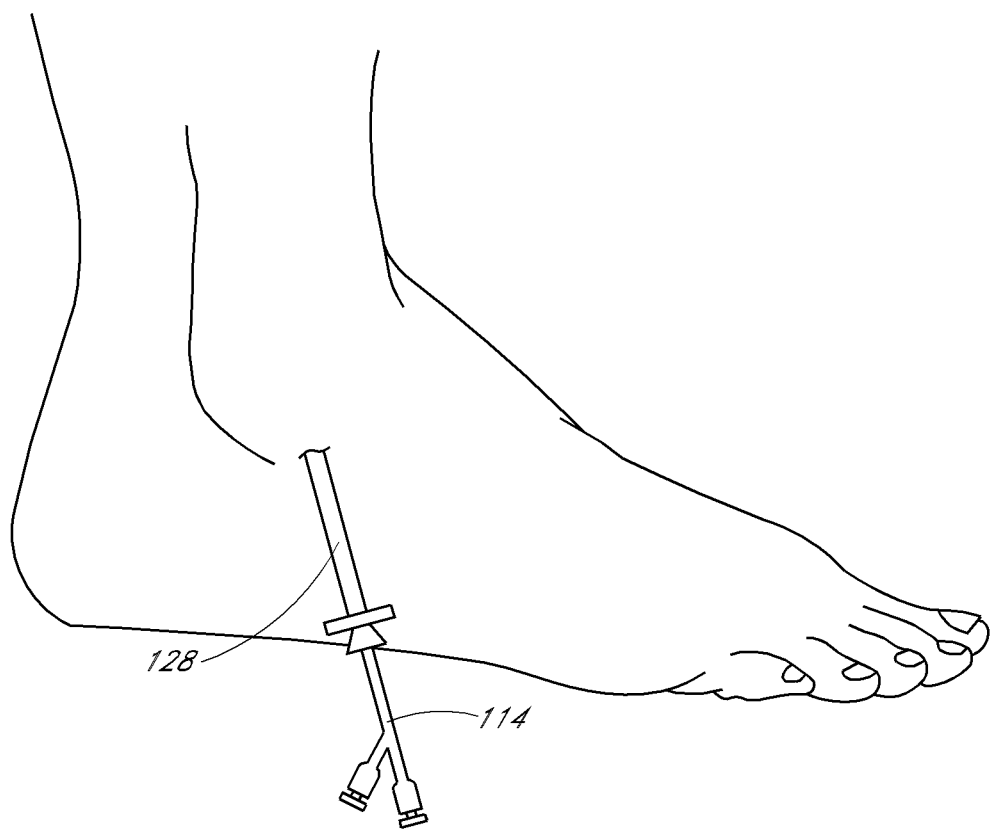
FIG. 29 is a side elevation view of a foot following insertion of the delivery catheter.

One indication for this embodiment of the implant and implantation procedure is a reducible, hyperpronated, flexible flatfoot. These patients are commonly pediatric, but adults with posterior tibial tendon dysfunction and/or hyperpronation in the absence of subtalar joint and mid tarsal joint arthritis are also potential candidates. FIG. 29 shows one procedure for using an embodiment of the implant comprises positioning the patient on a table and draping the lateral side of the foot in the usual sterile fashion known in the art. The insertion site for the implant is identified by palpation of bony markers, including but not limited to the fibular head, cuboid, talus and calcaneus bones. The lateral opening of the sinus tarsi is identified anterior, medial and inferior to the lateral malleolus or distal head of the fibula. Local anesthesia is injected into the skin and the connective tissue overlying the insertion site. Anesthetics with epinephrine may be used to limit bleeding at the insertion site. Alternatively, regional or general anesthesia may be used. The surgeon places the foot in a slightly supinated position to widen the lateral opening of the sinus tarsi during the procedure. A needle is inserted at the desired site and a small cannula is passed over the needle. The desired depth of insertion is determined by markings on the cannula and assisted by fluoroscopic imaging. The needle is then withdrawn. The cannula may be of "peel-away" type as is known to those with skill in the art. The foot with the inserted cannula is radiographically imaged to facilitate positioning of the cannula in the sinus tarsi. FIG. 28A illustrates sizing catheter 124 with an attached, fluid-filled syringe inserted through cannula 122. The foot is then repositioned and held in a generally neutral alignment. Neutral alignment is defined as the foot position where the lateral aspect of the heel becomes perpendicular to the leg and the talonavicular joint feels congruous to palpation. Neutral alignment is often, but not always, the position in the range of motion where the foot is capable of two-thirds additional supination and one-third additional pronation. Foot alignment can also be checked radiographically by assessing changes to the cyma lines in the AP and lateral views of the foot, as previously shown in FIGS. 9A and 10A.

Figure 28B:
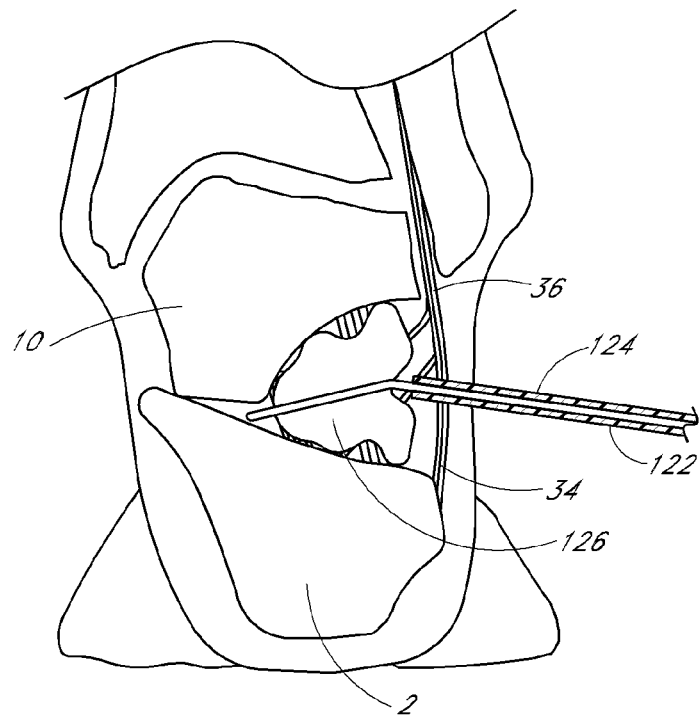
Figure 30A:
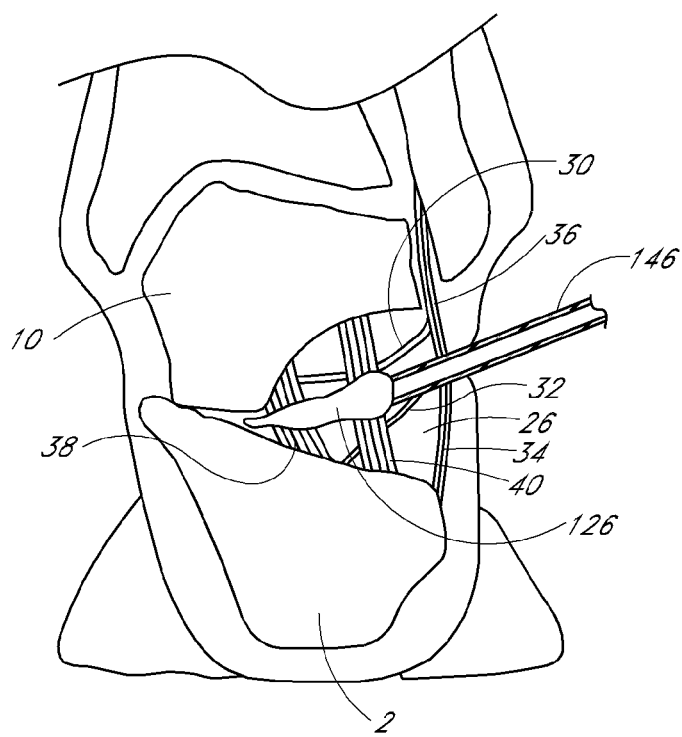
FIGS. 30A and 30B are schematic cross-sectional views of the foot with the implant inserted.
Figure 30B:
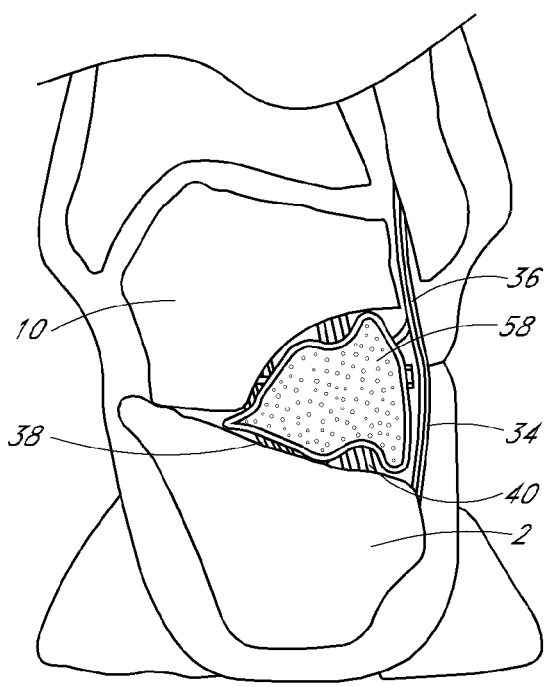

Referring to FIG. 28B, balloon tip 126 on sizing catheter 124 is inflated until significant resistance is met. The inflation volume on the syringe is measured. The surgeon assesses the range of motion and alignment of the foot with the inflated sizing catheter in place. This allows the surgeon to estimate the potential changes to the joint and to facilitate selection of the permanent implant. The surgeon also checks the quality, range, location and smoothness of joint motion. Radiographic imaging may be performed for additional assessment of the joint. The cannula is repositioned and/or the sizing balloon volume is adjusted to achieve approximately four degrees of foot eversion. As noted previously, approximately one third of the subtalar range should be in the direction of pronation and two-thirds towards supination. Balloon tip 126 is deflated and sizing catheter 124 is withdrawn. FIG. 30A shows delivery catheter 114 with selected inflatable implant 60 passed through cannula 122 and into sinus tarsi 26. Cannula 122 is optionally peeled away from the foot. Implant 60 is inflated with at least one material 58 to the desired volume based upon the inflation volume measured with sizing catheter 124. Foot alignment and range of motion is rechecked by physical exam and/or radiographic imaging. The inflation volume of implant 60 may be adjusted based upon the results of the exam and/or the imaging until the desired talocalcaneal position is achieved. In one embodiment, the surgeon uses the cyma line, in contradistinction to an anterior displaced talonavicular joint, as an indication that a pronated foot has been reduced to a more neutral alignment. Implant 60 is then sealed, if implant 60 is not self-sealing. Referring to FIG. 30B, delivery catheter 114 is detached from implant 60 and both catheter 114 and cannula 122 are withdrawn from the patient. If necessary, the insertion site is closed by either suturing or adhesives and dressed. A splint or cast is applied to the foot.

In an alternative implantation procedure, the material used to inflate implant 60 to the desired volume is removed from the implant and its volume is measured. An equal or similar volume of another material having a different density or characteristics is used to reinflate the implant. This alternative procedure may be used to obtain a more accurate measurement of the sinus tarsi and the volume of final inflation material to be used where the final inflation material changes volume as it cures. The volume of the initial fluid used to assess the sinus tarsi is used to calculate the volume of uncured final inflation material to be delivered.

In another alternate method of implanting the device using a guidewire, the patient is placed on a table and the lateral side of the foot is draped in the usual sterile fashion known in the art. The insertion site for the device is identified by palpation of bony markers, including but not limited to the fibular head, cuboid, talus and calcaneus bones. Local anesthesia is injected into the skin and connective tissue overlying the insertion site. Anesthetics with epinephrine may be used to limit bleeding at the insertion site. A large bore needle is inserted at the desired site and a guidewire is passed through the needle. Optionally, a small dilator is passed over the guidewire for enlarging the pathway to the sinus tarsi. The foot with the inserted guidewire is radiographically imaged to confirm positioning of the guidewire in the sinus tarsi. A catheter with the inflatable implant at the catheter tip is passed over the guidewire and into the sinus tarsi. The implant is inflated to the desired volume. The talo-calcaneal relationship is checked by physical exam and/or radiographic imaging. The inflation volume of the implant may be adjusted based upon the results of the exam and/or the imaging until the desired talo-calcaneal position is achieved. The surgeon may use the cyma line, in contradistinction to an anterior displaced talo-navicular joint, as an indication that a pronated foot has been reduced to a more neutral alignment. The delivery catheter is detached from the implant and both the catheter and guidewire are withdrawn from the patient. The insertion site is closed by either suturing or adhesives and dressed.

Figure 31A:
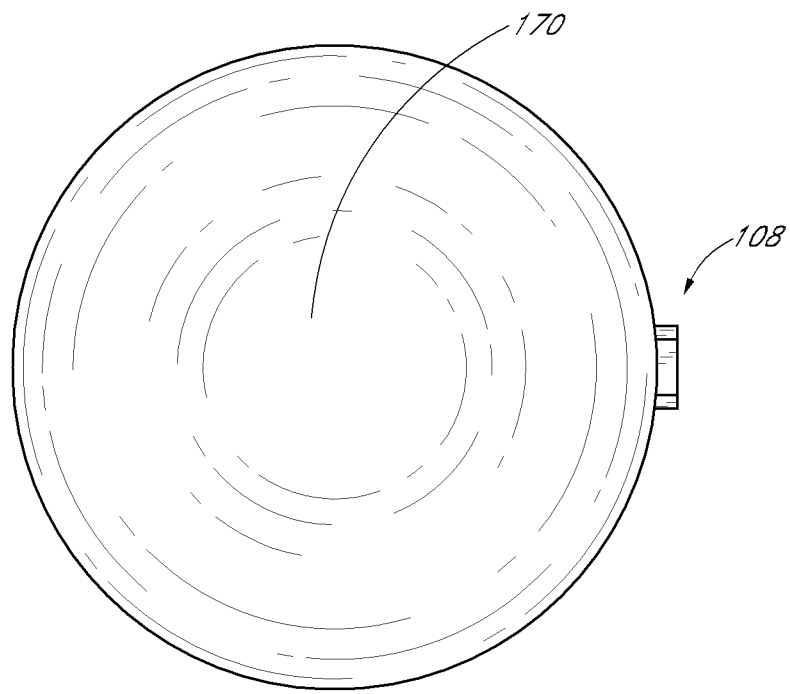
FIG. 31A is a front elevation view of one embodiment of a first MTP joint inflatable implant and FIG. 31B is a side cross-sectional view of the implant in FIG. 31A.
Figure 31B:
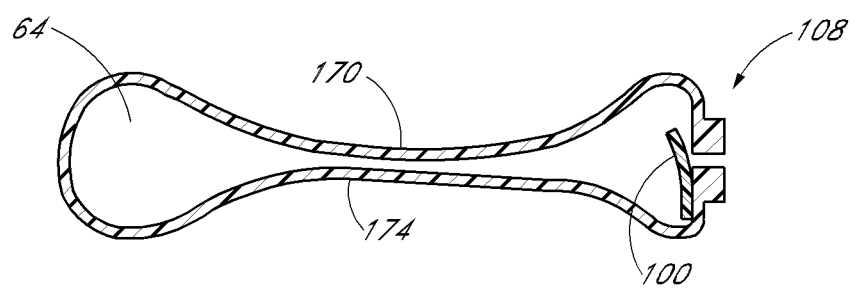

The implant and delivery system described above can also be adapted for insertion into the first MTP joint of the foot. Referring to FIGS. 31A and 31B, the implant shape for this embodiment of the invention is preferably an implant comprising a first concave surface 170 on a first side of the implant 172 and a second concave surface 174 on a second side. First concave surface 170 is adapted to contact the distal end of the first metatarsal and second concave surface 176 is adapted to contact the proximal end of the first proximal phalanx of the foot. Other shapes, however, can be used depending upon the particular anatomy and disease of the first MTP joint. The delivery system will generally have a shorter length because of the accessibility of the first MTP joint.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of treating a patient, comprising the steps of:
   accessing a sinus tarsi of a foot through an access path having a cross sectional diameter of no more than about 0.5 inches, the sinus tarsi having a talus and calcaneus spaced apart by a first minimum distance;
   positioning a sizing balloon within the sinus tarsi;
   inflating the sizing balloon with a volume of inflation media, thereby increasing the space between the talus and calcaneus to a second minimum distance;
   removing the sizing balloon; and thereafter
   inflating an implant in the sinus tarsi with a curable media having a volume equal to the volume of said inflation media thereby restraining the talus and calcaneus at said second minimum distance.

* * * * *